United States Patent [19]

Sudilovsky

[11] Patent Number: 5,015,633

[45] Date of Patent: May 14, 1991

[54] METHOD FOR INHIBITING LOSS OF COGNITIVE FUNCTIONS EMPLOYING AN ACE INHIBITOR

[75] Inventor: Abraham Sudilovsky, Lawrenceville, N.J.

[73] Assignee: E. R. Squibb & Sons, Inc., Princeton, N.J.

[21] Appl. No.: 308,293

[22] Filed: Feb. 9, 1989

Related U.S. Application Data

[63] Continuation-in-part of Ser. No. 160,989, Feb. 26, 1988, abandoned, which is a continuation-in-part of Ser. No. 118,121, Nov. 9, 1987, abandoned, which is a continuation-in-part of Ser. No. 43,127, Apr. 27, 1987, abandoned.

[51] Int. Cl.$^5$ ............................................. A61K 37/00
[52] U.S. Cl. ....................................... 514/91; 514/7; 514/19; 514/89; 514/92; 514/94; 514/171; 514/212; 514/218; 514/312; 514/338; 514/343; 514/409; 514/422; 514/423; 514/616; 514/693
[58] Field of Search ................. 514/7, 19, 89, 91, 92, 514/94, 171, 212, 218, 312, 338, 223.5, 249, 255, 278, 318, 343, 409, 422, 423, 616, 693; 548/413

[56] References Cited

U.S. PATENT DOCUMENTS 4,452,790  6/1984  Karanewky ..................... 548/112

FOREIGN PATENT DOCUMENTS 3601391  3/1986  Fed. Rep. of Germany .

OTHER PUBLICATIONS

Sudilovsky et al., "Captopril Delays Extinction of Conditional Avoidance Response in the Rat", Poster Presentation 14th Congress of the Collegium Internationale Neuro-Psychopharmacologicum, Florence Italy, Jun. 1984.
Melo, J. C. et al., J. Pharmacol., 193:1–9 (1975).
Morgan, J. M. et al., Science, 196:87–89 (1977).
Koller, M. et al., Neuroscience Letters, 14:71–75 (1979).
Evered, M. D. Eurp. J. Pharmacol., 68:443–449 (1980).
Marson, O. et al., Brazil, J. Med. Biol. Res., 14:73–76 (1981).
Arregui, A et al., J. Neurochem., 103:1490–1492 (1982).
Scholkens, B. A. et al., Clin. Exper. Hyper.–Theor. Pract., A5;1301–1317 (1983).
Mann, J. F. E. et al. Clin. Sci., 56:585–589 (1979).
Vollmer, R. R. et al., Europ. J. Pharmacol., 45:117–125 (1977).
"The Effects of Antihypertensive Therapy on the Quality of Life" by S. H. Croog et al. New England Journal of Medicine, 314:1657–1664 (Jun. 26), 1986.
"Angiotensin Converting Enzyme Inhibitors: Animal Experiments Suggest a New Pharmacological Treatment for Alcohol Abuse in Humans" by G. Spinosa et al., Alcoholism: Clinical and Experimental Research, vol. 12, No. 1, Jan./Feb. 1988, pp. 65–70.
"Alcohol Satiety, Hypertension and the Renin–Angiotensin System" by L. A. Grupp, Medical Hypothese (1987) 24, 11–19 (Longman Group UK Ltd. 1987).

*Primary Examiner*—Lester L. Lee
*Attorney, Agent, or Firm*—Burton Rodney

[57] ABSTRACT

A method is provided for inhibiting loss of cognitive function, including memory, which may or may not be associated with Alzhemier's disease, in a mammalian species by administering an ACE inhibitor, which is a phosphonate substituted amino or imino acid or salt, such as SQ 29,852 over a prolonged period of treatment.

5 Claims, 19 Drawing Sheets

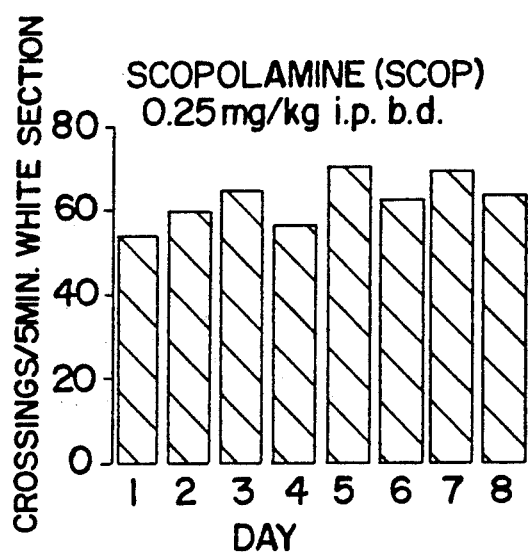
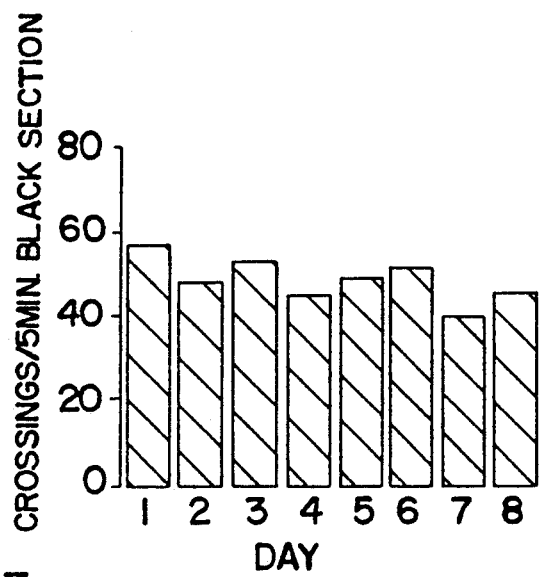
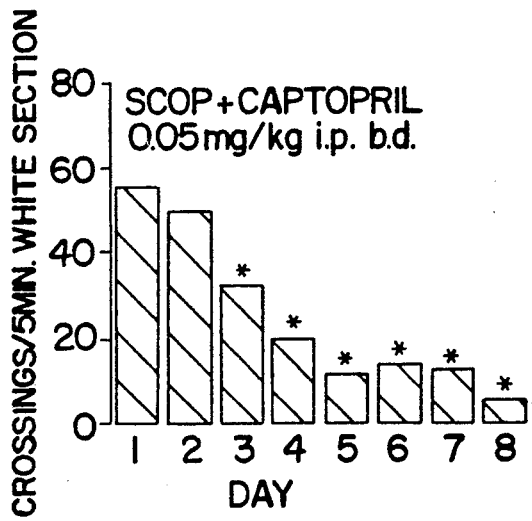
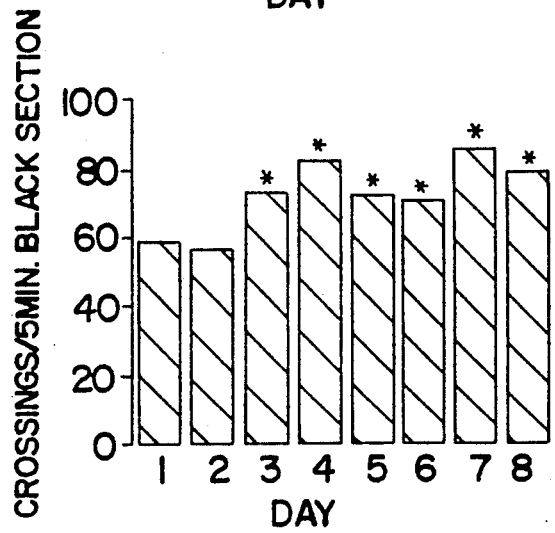
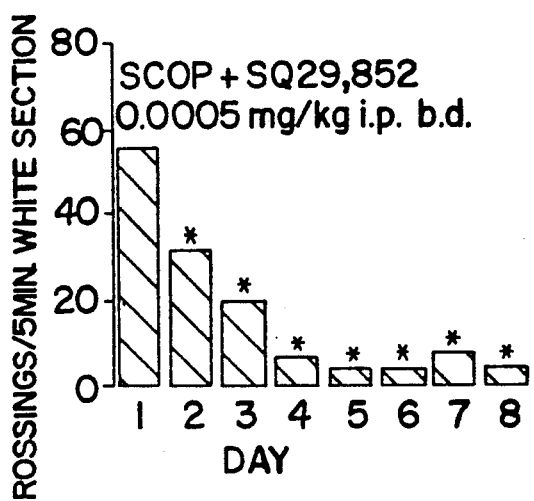
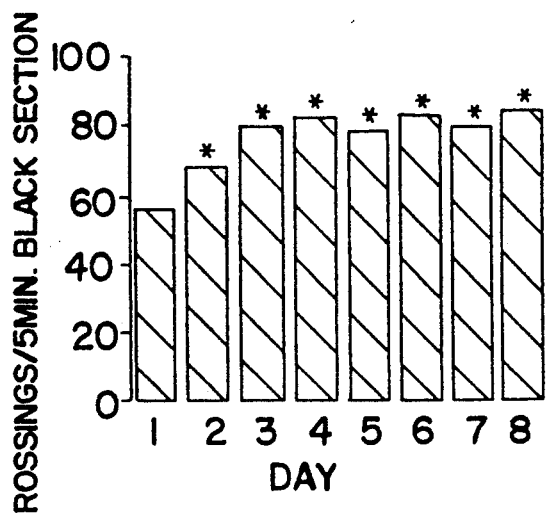
FIG.3

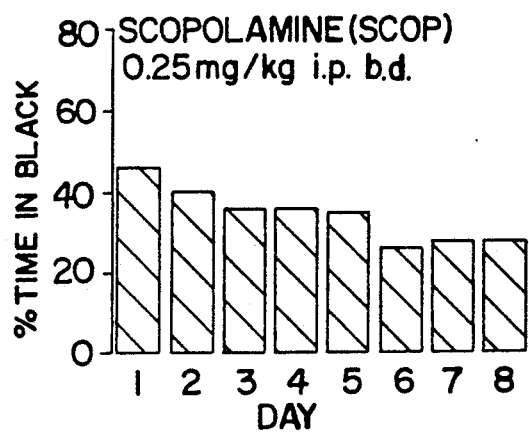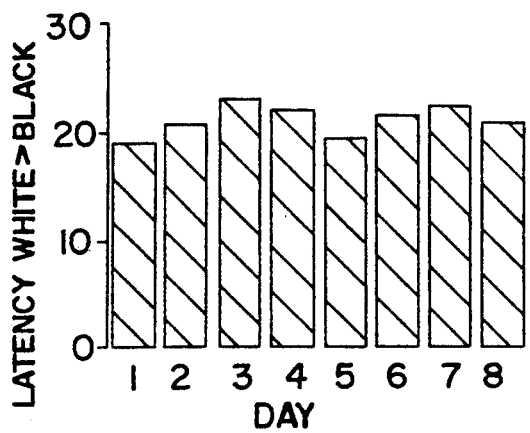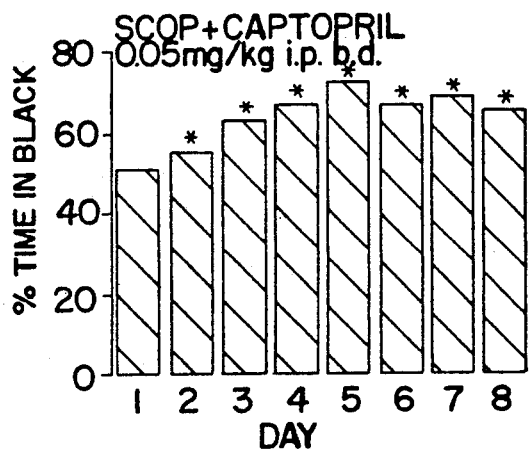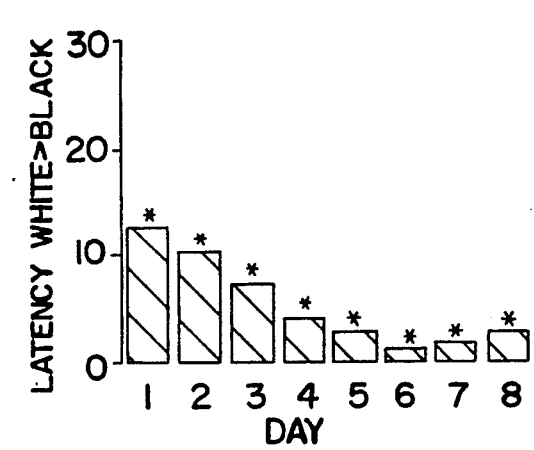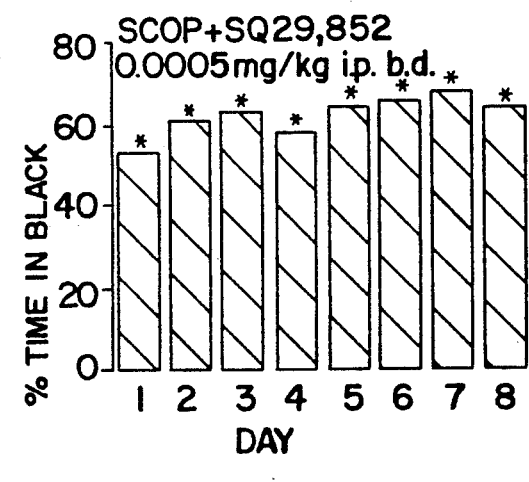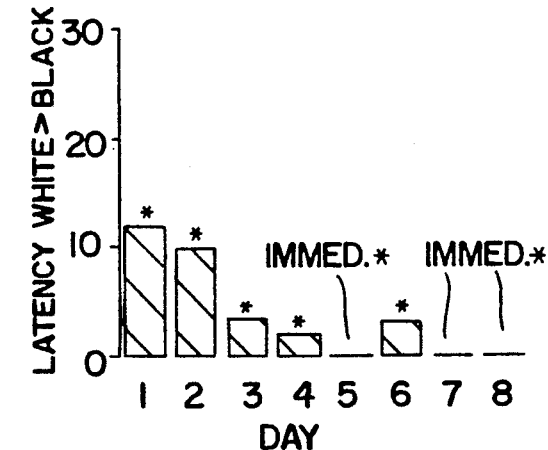
FIG.4

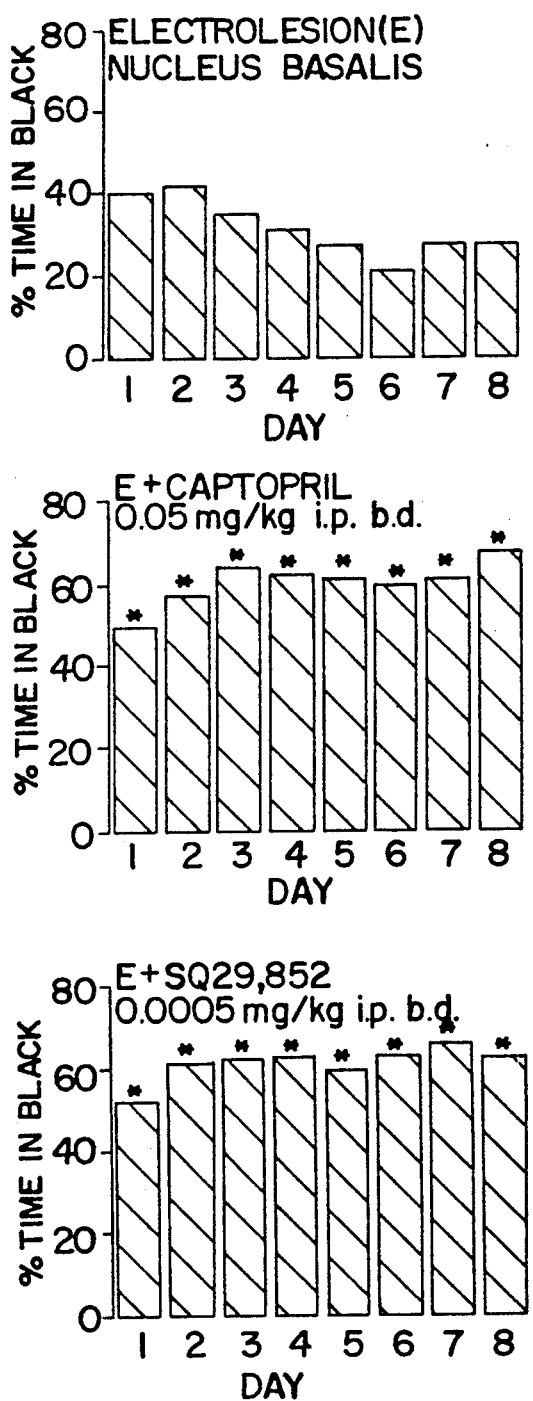
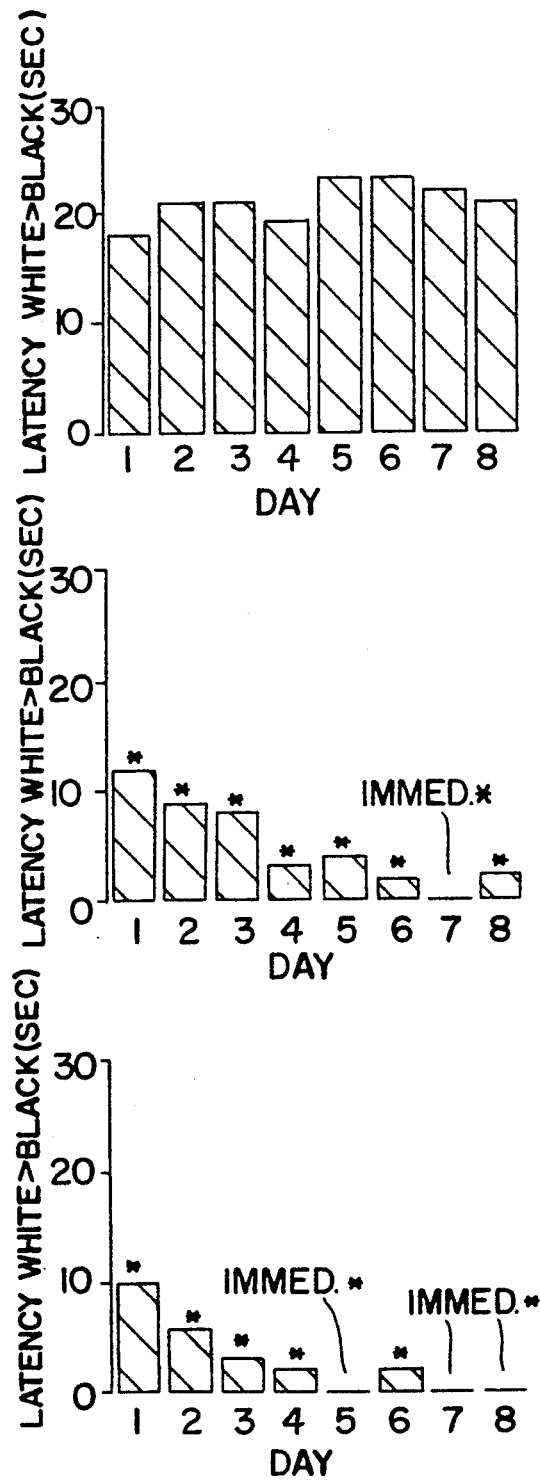
FIG.7

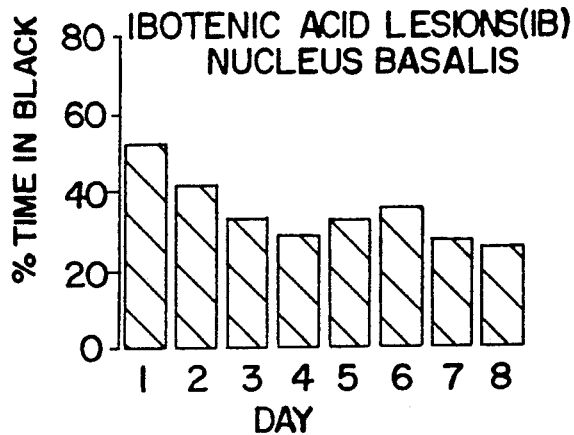
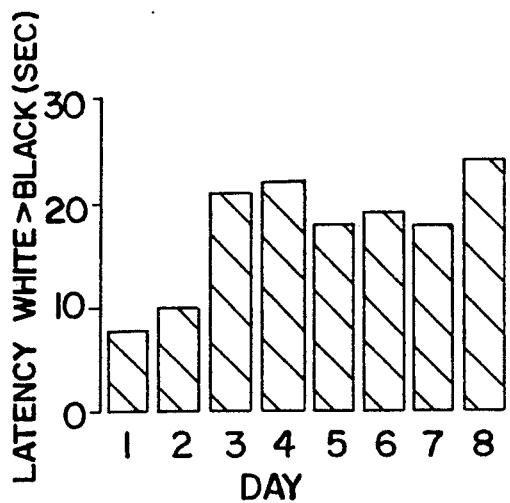
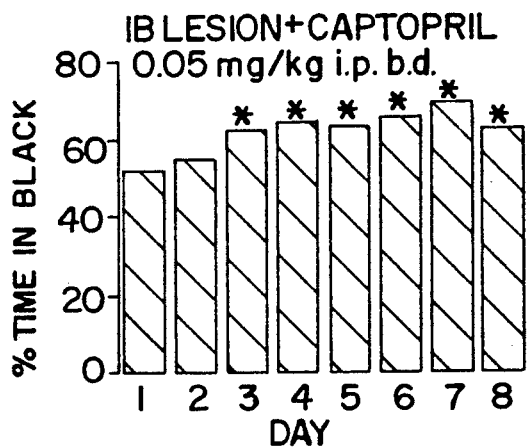
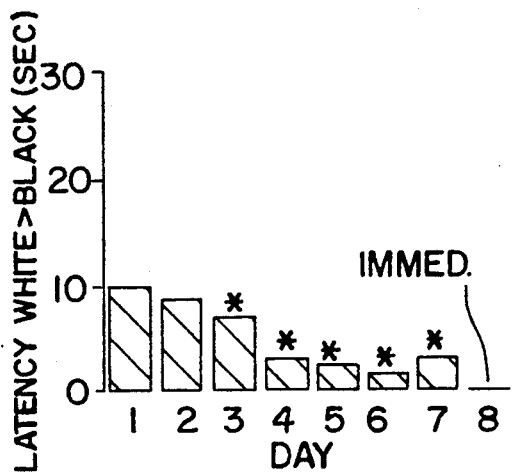
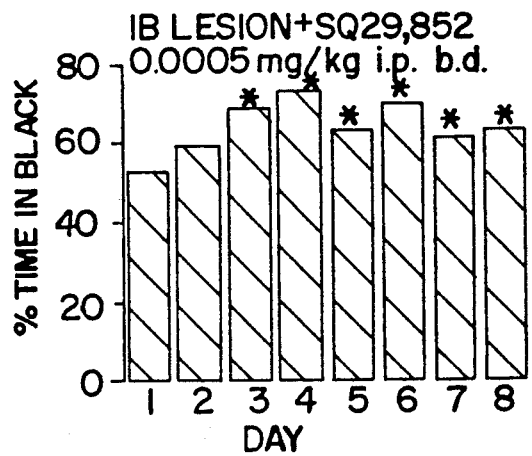
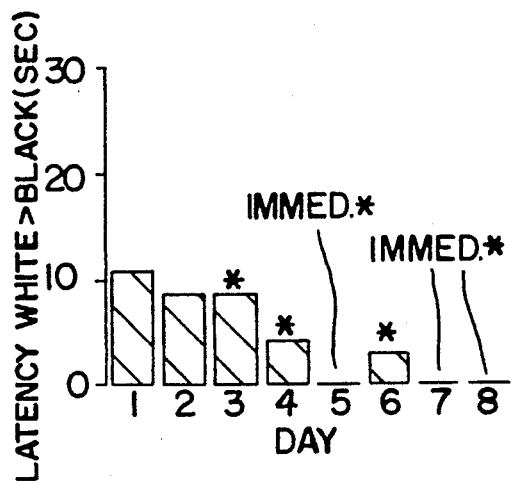
FIG.10

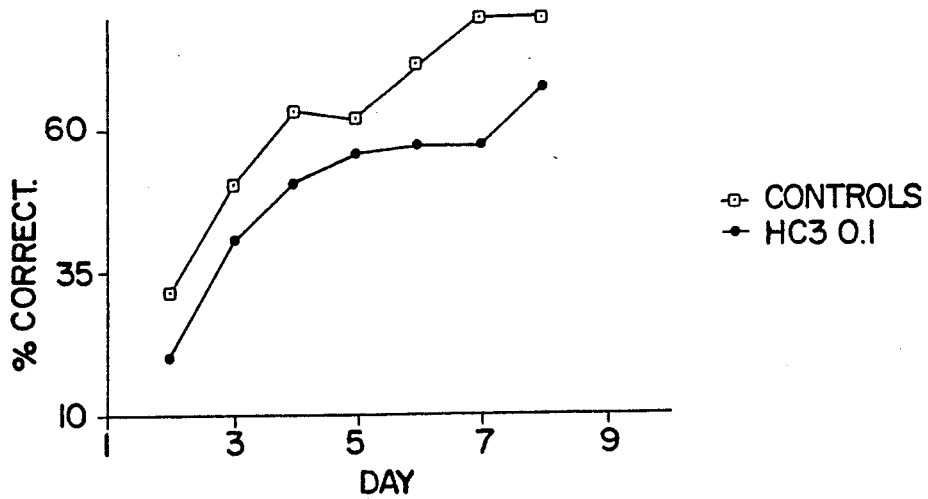
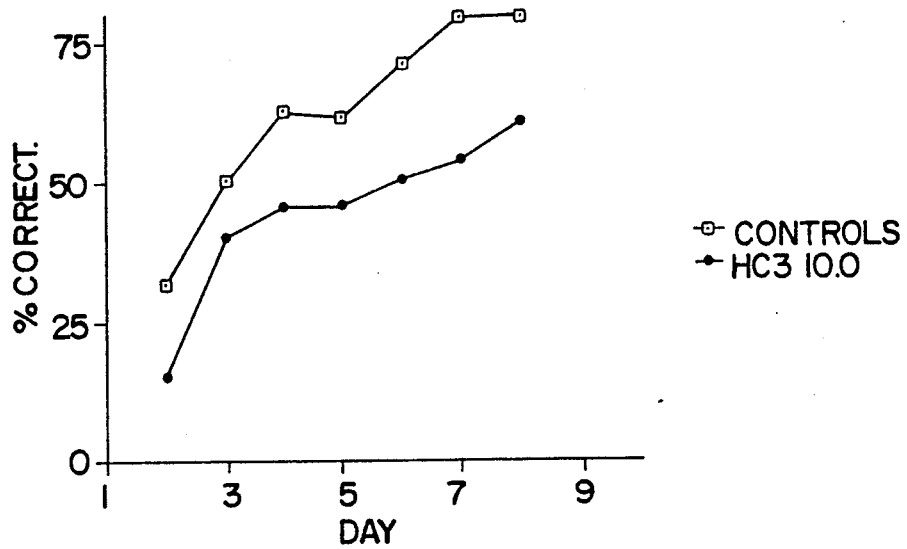
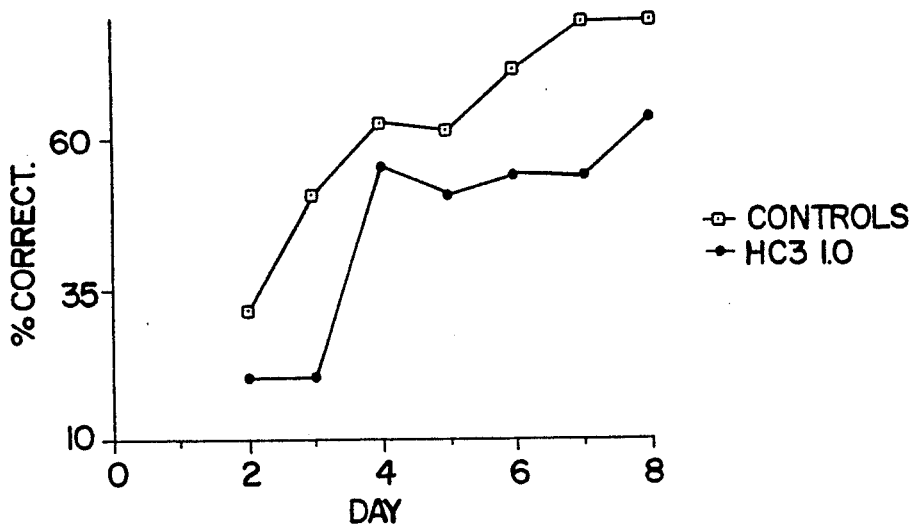
FIG.15

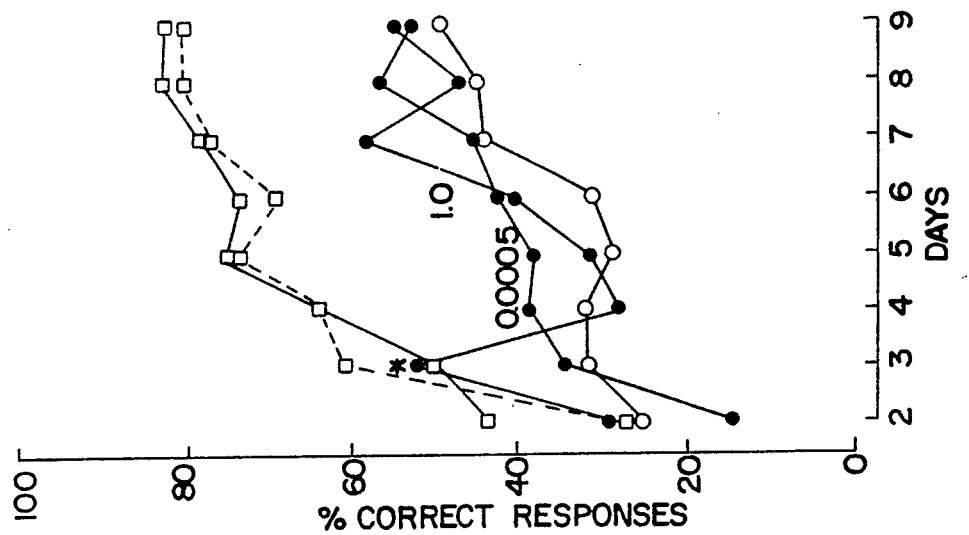
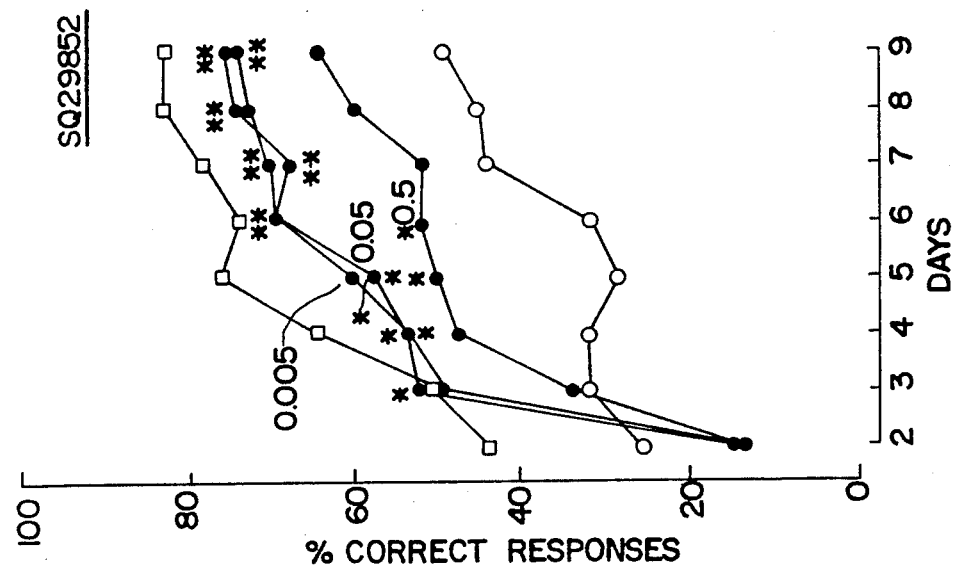
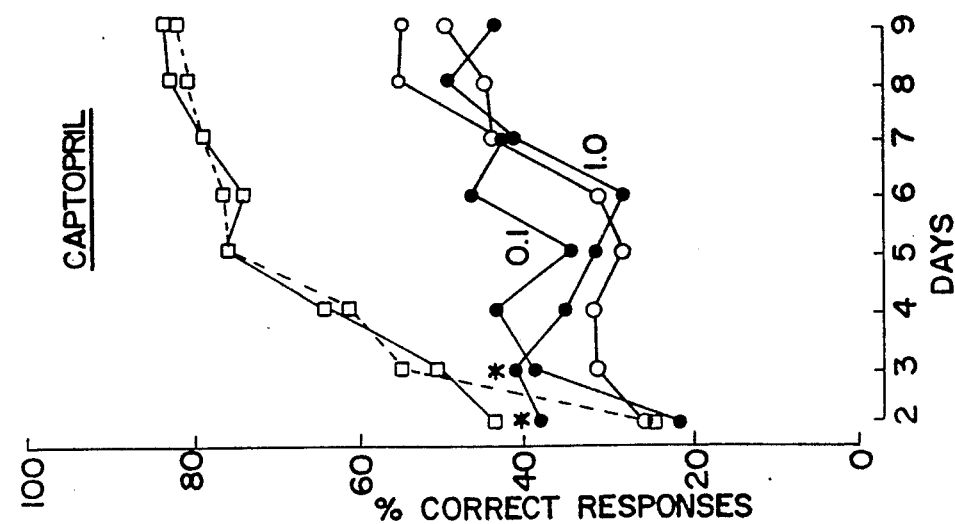
FIG. 17

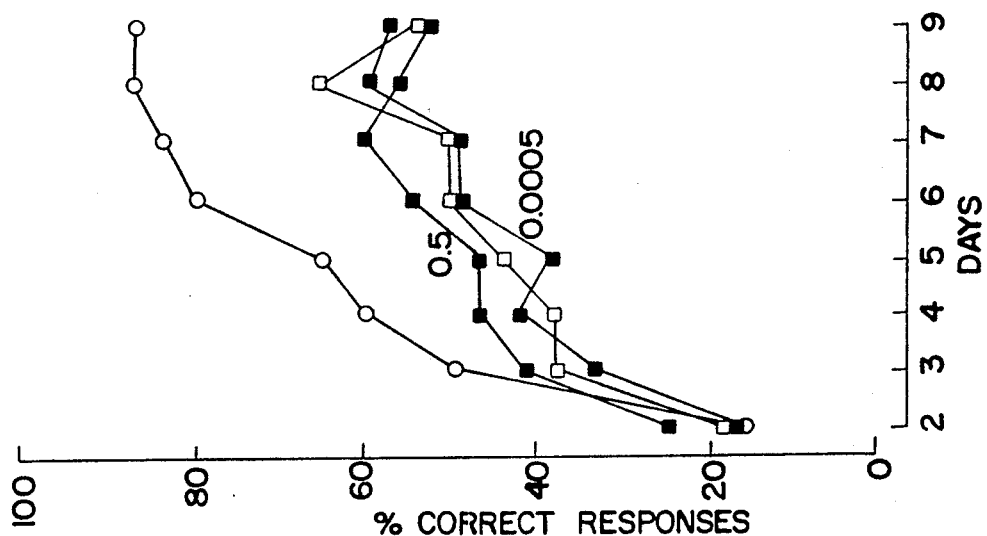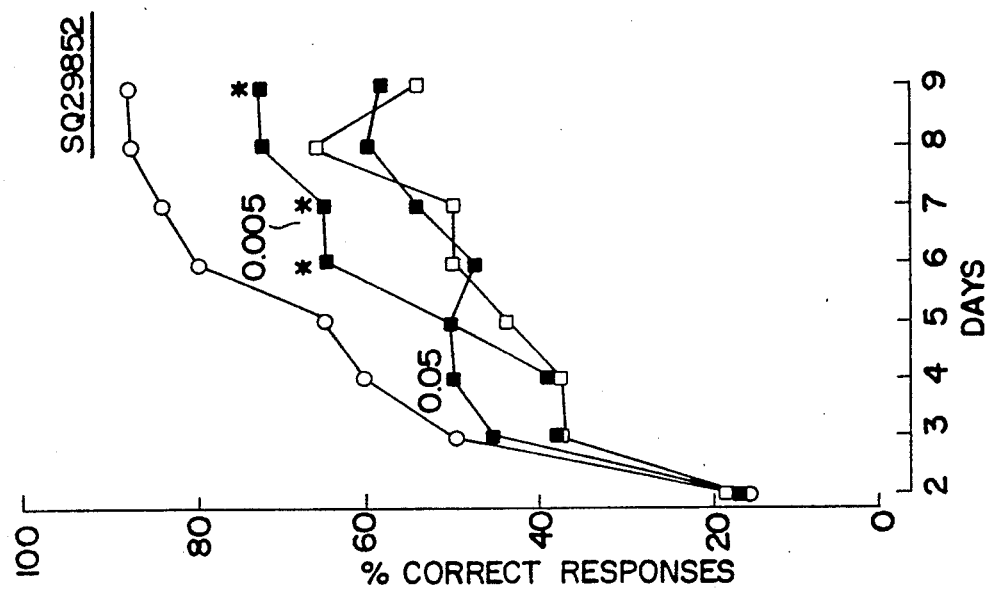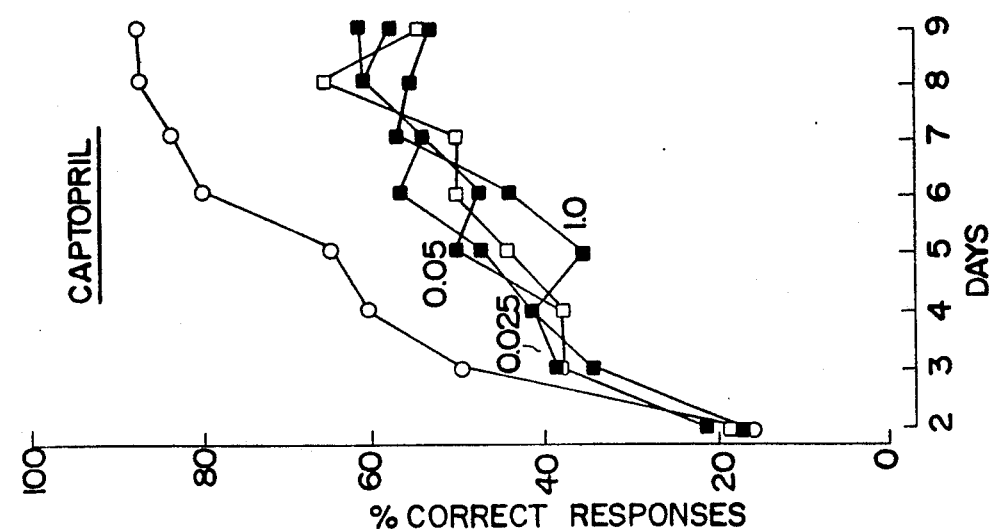
FIG.18

METHOD FOR INHIBITING LOSS OF COGNITIVE FUNCTIONS EMPLOYING AN ACE INHIBITOR

REFERENCE TO OTHER APPLICATIONS

This application is a continuation-in-part of U.S. patent application Ser. No. 160,989, filed Feb. 26, 1988 and now abandoned, which is a continuation-in-part of U.S. patent application Ser. No. 118,121, filed Nov. 9, 1987, now abandoned, which is a continuation-in-part of U.S. patent application Ser. No. 43,127, filed Apr. 27, 1987, now abandoned.

DESCRIPTION OF THE INVENTION

In accordance with the present invention, a method is provided for inhibiting loss of cognitive functions such as memory, attention span, concentration and ability to learn or for treating or delaying progression of Alzheimer's disease or other types of dementias and/or memory disorders, including age-associated memory impairment (all of which are included under the term cognitive function), in mammalian species over a prolonged period wherein a therapeutically effective amount of an angiotensin converting enzyme inhibitor which is a phosphonate substituted amino or imino acid or salt thereof, such as SQ29,852, which is systemically; such as orally or parenterally, administered over a prolonged period, to inhibit loss of cognitive function during such period.

The method of the invention is useful in treating or delaying progression of primary degeneration dementias arising in the senium and presenium such as Alzheimer's disease, Pick's disease and Binswanger's disease, and vascular dementias such as arteriosclerotic dementias including multiple infarct dementia and Binswanger's disease.

The angiotensin converting enzyme inhibitor which may be employed herein includes any of the phosphonate substituted amino or imino acids or salts disclosed in U.S. Pat. No. 4,452,790 with (S)-1-[6-amino-2-[[hydroxy (4-phenylbutyl)phosphinyl]oxy]-1-oxohexyl]-L-proline (SQ 29,852 being preferred.

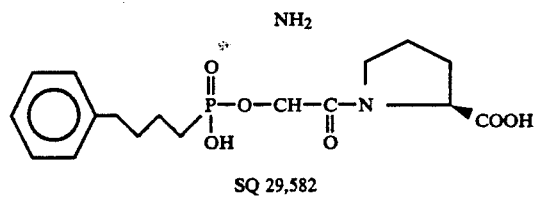

SQ 29,582

U.S. Pat. No. 4,452,790 to Karanewsky et al is directed to angiotensin converting enzyme inhibitors which are phosphonate substituted amino or imino acids and salts thereof having the formula

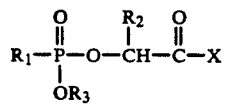

wherein X is an imino or amino acid of the formula

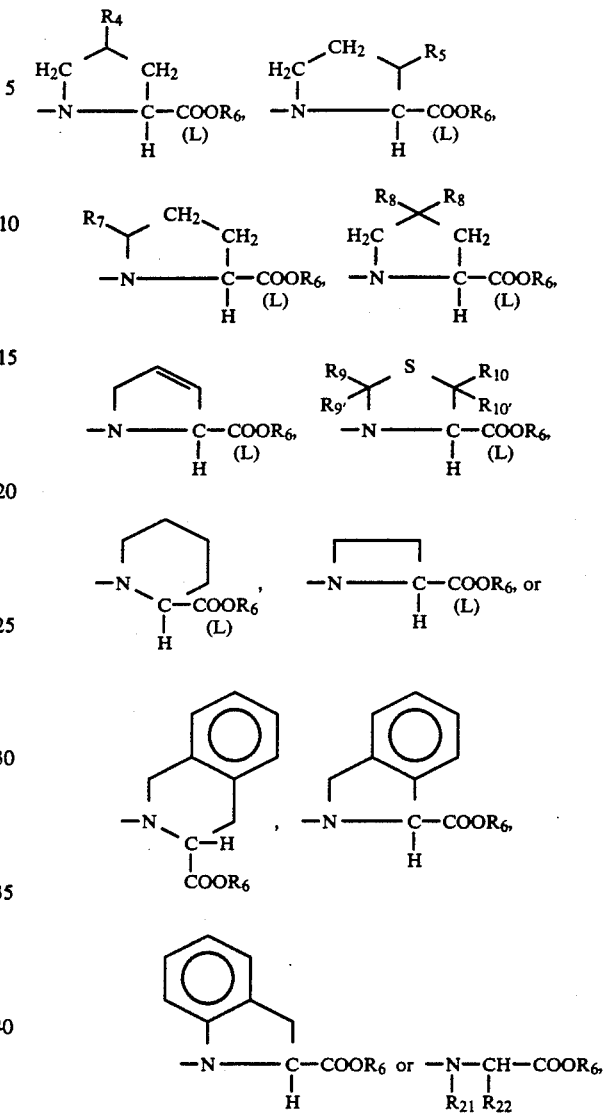

$R_4$ is hydrogen, lower alkyl, halogen, keto, hydroxy,

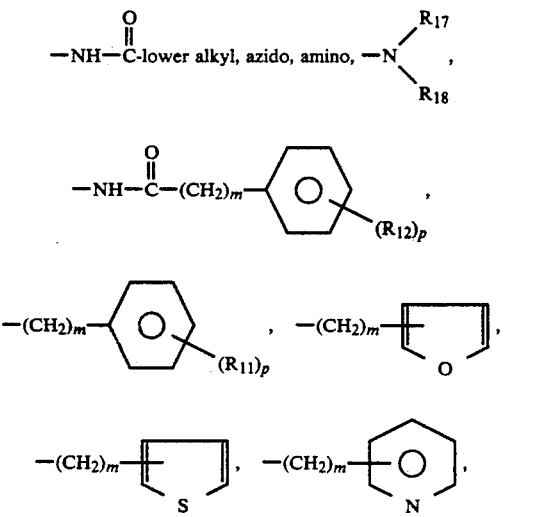

a 1- or 2-naphthyl of the formula

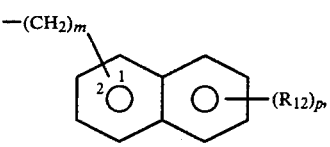

—(CH$_2$)$_m$-cycloalkyl, —O—C(=O)—N(R$_{13}$)(R$_{13}$), —O-lower alkyl,

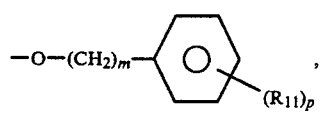

a 1- or 2-naphthyloxy of the formula

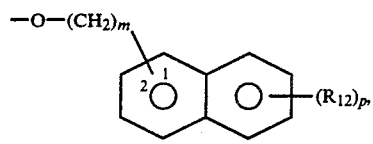

—S-lower alkyl,

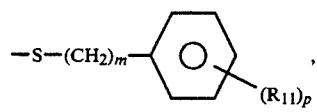

or a 1- or 2-naphthylthio of the formula

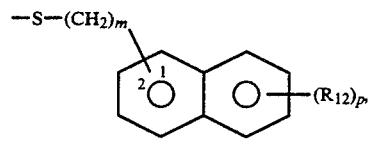

R$_5$ is keto, halogen, —O—C(=O)—N(R$_{13}$)(R$_{13}$),

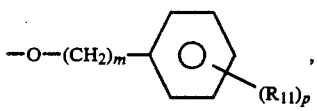

—O-lower alkyl, a 1- or 2-naphthyloxy of the formula

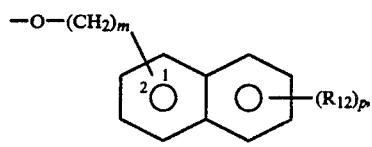

—S-lower alkyl,

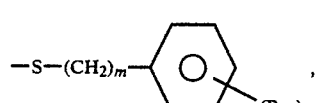

or a 1- or 2-naphthylthio of the formula

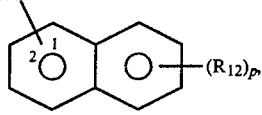

R$_7$ is keto or

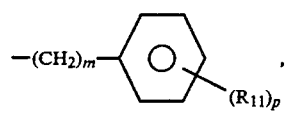

Each R$_8$ is independently halogen or —Y—R$_{14}$.

R$_9$, R$_9'$, R$_{12}$ and R$_{10}'$ are independently selected from hydrogen and lower alkyl or R$_9'$, R$_{10}$ and R$_{10}'$ are hydrogen and R$_9$ is

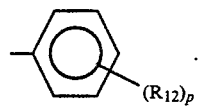

R$_{11}$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl.

R$_{12}$ is hydrogen, lower alkyl of 1 to 4 carbons, lower alkoxy of 1 to 4 carbons, lower alkylthio of 1 to 4 carbons, chloro, bromo, fluoro, trifluoromethyl or hydroxy.

m is zero, one, two or three.

p is one, two or three provided that p is more than one only if R$_{11}$ or R$_{12}$ is hydrogen, methyl, methoxy, chloro or fluoro.

R$_{13}$ is hydrogen or lower alkyl of 1 to 4 carbons.

Y is oxygen or sulfur.

R$_{14}$ is lower alkyl of 1 to 4 carbons,

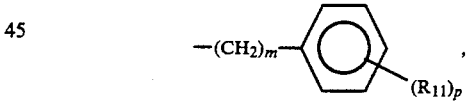

or the R$_{14}$ groups join to complete an unsubstituted 5 or 6-membered ring or said ring in which one or more of the carbons has a lower alkyl of 1 to 4 carbons or a di(lower alkyl of 1 to 4 carbons) substituent.

R$_{21}$ is hydrogen, lower alkyl, cycloalkyl, phenyl or

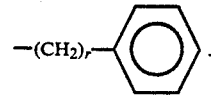

R$_{22}$ is hydrogen, lower alkyl,

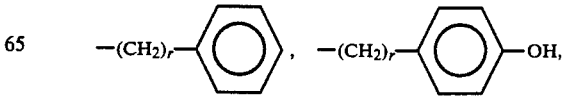

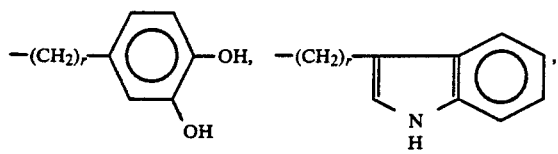
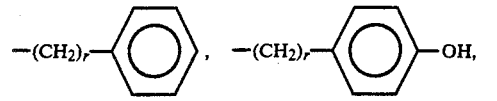
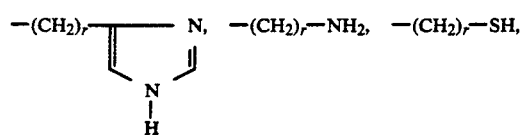
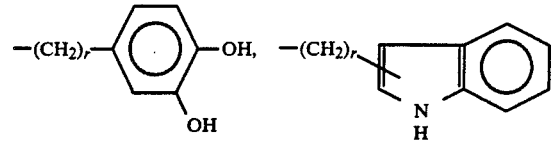
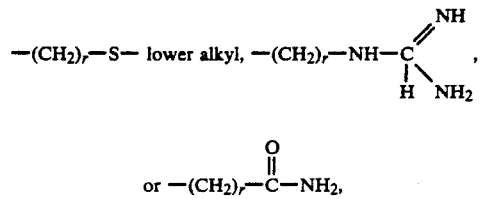
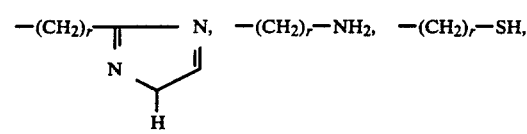

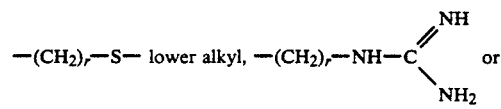

r is an integer from 1 to 4.

R₁ is alkyl of 1 to 10 carbons, aminoalkyl, haloalkyl,

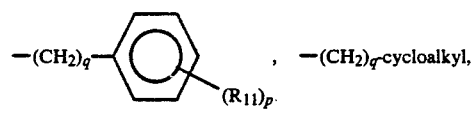
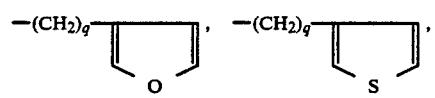
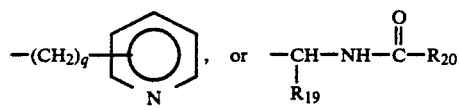

wherein q is zero or an integer from 1 to 7 and R₁₂ and p are as defined above.

R₁₉ and R₂₀ are independently selected from hydrogen, lower alkyl, halo substituted lower alkyl,

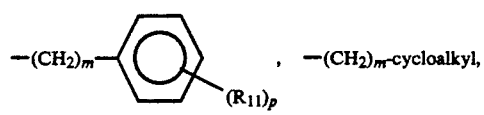
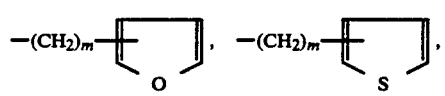
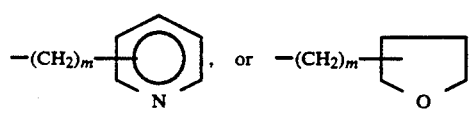

wherein m, R₁₁, and p are as defined above.

R₂ is hydrogen, lower alkyl, halo substituted lower alkyl, wherein r is as defined above.

R₃ and R₆ are independently selected from hydrogen, lower alkyl, benzyl, alkali metal such as Li, Na or K, benzhydryl, or

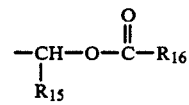

wherein R₁₅ is hydrogen, lower alkyl, cycloalkyl or phenyl, and R₁₆ is hydrogen, lower alkyl, lower alkoxy, phenyl, or R₁₅ and R₁₆ taken together are —(CH₂)₂—, —(CH₂)₃—, —CH=CH—, or

R₁₇ is lower alkyl, benzyl, or phenethyl.

R₁₈ is hydrogen, lower alkyl, benzyl or phenethyl.

The disclosure of the above-mentioned patent is incorporated herein by reference.

In carrying out the method of the present invention, the angiotensin converting enzyme inhibitor as defined above may be administered to mammalian species, such as monkeys, dogs, cats, rats, humans, etc. and as such may be incorporated in a conventional systemic dosage form, such as a tablet, capsule, elixir or injectable. The above dosage forms will also include the necessary carrier material, excipient, lubricant, buffer, antibacterial, bulking agent (such as mannitol), anti-oxidants (ascorbic acid of sodium bisulfite) or the like. Oral dosage forms are preferred, although parenteral forms are quite satisfactory as well.

With regard to such systemic formulations, single or divided doses of from about 0.1 to about 500 mg, preferably from about 1 to 100 mg/one to four times daily, may be administered in systemic dosage forms as described above for a prolonged period, that is, for as long as inhibition of loss of cognitive function is to continue. Sustained release forms of such formulations which may provide such amounts biweekly, weekly, monthly and the like may also be employed. A dosing period of at least one week is required to achieve minimal benefit.

BRIEF DESCRIPTION OF THE FIGURES

FIGS. 2 to 4 are graphs showing ability of captopril and SQ29,852 to improve mouse habituation performance during continuous scopolamine administration;

FIGS. 5 to 7 are graphs showing ability of captopril and SQ29,852 to improve mouse habituation performance following nucleus basalis lesions (electrolesion);

FIGS. 8 to 10 are graphs showing ability of captopril and SQ29,852 to improve mouse habituation performance following nucleus basalis lesions (ibotenic acid);

FIGS. 13, 14 and 15 are graphs showing the effect of SQ29,852, captopril and ICV HC3, respectively, on choice performance;

FIG. 17 is a graph showing the effects of captopril and SQ29,852 on scopolamine induced impairment in a T-maze reinforced alternation task in the rat;

FIG. 18 is a graph showing the effects of captopril and SQ29,852 in aged rats in a T-maze reinforced alternation task.

Figure 1:
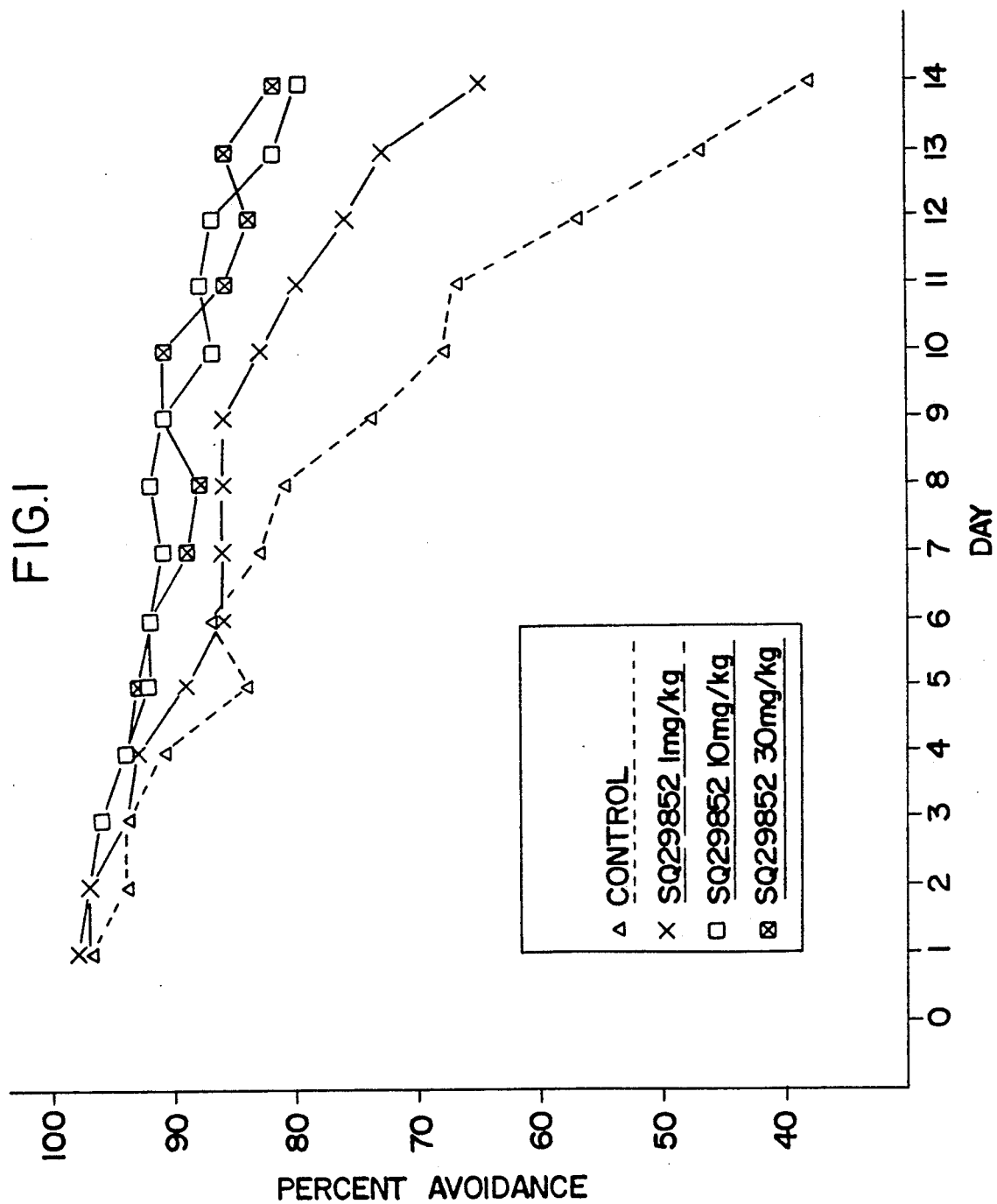
FIG. 1 is a graph of mean percent of shuttle avoidance responding in male rats one hour after intraperitoneal administration of SQ29,852 at 1 mg/kg, 10 mg/kg and 30 mg/kg and saline versus days of treatment.

The following Examples represent preferred embodiments of the present invention.

EXAMPLE 1

An SQ29,852 formulation suitable for oral administration in inhibiting loss of cognitive functions is set out below.

1000 tablets each containing 100 mg of (S)-1-[6-amino-2-[[hydroxy(4-phenylbutyl)phosphinyl]oxy-1-oxohexyl]-L-proline were produced from the following ingredients.

| | |
|---|---|
| (S)-1-[6-Amino-2-[[hydroxy(4-phenyl-butyl)phosphinyl]oxy-1-oxohexyl]-L-proline (SQ29,852) | 100 g |
| Corn starch | 50 g |
| Gelatin | 7.5 g |
| Avicel (microcrystalline cellulose) | 25 g |
| Magnesium stearate | 2.5 g |

The SQ29,852 and corn starch are admixed with an aqueous solution of the gelatin. The mixture is dried and ground to a fine powder. The Avicel and then the magnesium stearate are admixed with the granulation. This is then compressed in a tablet press to form 1000 tablets each containing 100 mg of active ingredient which is used for inhibiting loss of cognitive functions.

By substituting 100 g of the ACE inhibitor (±)-1-[2-[[hydroxy(4-phenylbutyl)phosphinyl]oxy]-1-oxopropyl]-L-proline, dilithium salt for the SQ 29,852 in Example 1, 1000 tablets each containing 100 mg of such ACE inhibitor are produced which is useful in inhibiting loss of cognitive functions.

EXAMPLE 3

1000 tablets each containing 200 mg of ACE inhibitor are produced from the following ingredients:

| | |
|---|---|
| 1-[(S)-2-[[[(±)-1-Benzoylamino-3-phenylpropyl]phosphinyl]oxy]-1-oxopropyl]-L-proline, dilithium salt (ACE inhibitor) | 200 g |
| Lactose | 100 g |
| Avicel | 150 g |
| Corn starch | 50 g |
| Magnesium stearate | 5 g |

The ACE inhibitor, lactose and Avicel are admixed, then blended with the corn starch. Magnesium stearate is added. The dry mixture is compressed in a tablet press to form 1000 505 mg tablets each containing 200 mg of active ingredient. The tablets are coated with a solution of Methocel E 15 (methyl cellulose) including as a color a lake containing yellow #6. The resulting tablets are useful in inhibiting loss of cognitive functions.

EXAMPLE 4

Two piece #1 gelatin capsules each containing 250 mg of ACE inhibitor are filled with a mixture of the following ingredients:

| | |
|---|---|
| (±)-1-[2-[[[(2,2-Dimethyl-1-oxopropoxy)methoxy](4-phenylbutyl)phosphinyl]-oxy]-1-oxopropyl]-L-proline | 250 mg |
| Magnesium stearate | 7 mg |
| USP lactose | 193 mg. |

The resulting capsules are useful in inhibiting loss of cognitive functions.

EXAMPLE 5

An injectable solution for use in inhibiting loss of cognitive functions is produced as follows:

| | |
|---|---|
| SQ29, 852 | 500 mg |
| Methyl paraben | 5 mg |
| Propyl paraben | 1 mg |
| Sodium chloride | 25 g |
| Water for injection qs. | 5 l. |

The SQ29,852 preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains 5 ml of solution in a concentration of 100 mg of active ingredient per ml of solution for injection.

EXAMPLE 6

Tablets for use in inhibiting loss of cognitive functions are prepared as described in Example 1 except that (±)-1-[2-[[hydroxy(4-phenylbutyl) phosphinyl]oxy]-1-oxopropyl]-L-proline, disodium salt is used in place of SQ 29,852.

EXAMPLE 7

The following experiments were carried out to demonstrate the effectiveness of the ACE inhibitor SQ29,852 to improve cognition and cognitive impairment.

Techniques used:

a) Ability to improve basic performance and to antagonize a scopolamine impairment in a mouse habituation test.

b) Ability to improve basic performance and to antagonize a scopalamine impairment in a food reinforced alternation task in the rat using an elevated T maze.

c) Ability to improve discriminative and reverse learning in the marsoset using the Wisconsin General Test Apparatus.

a) ABILITY TO IMPROVE BASIC PERFORMANCE AND TO ANTAGONIZE A SCOPOLAMINE IMPAIRMENT IN A MOUSE HABITUATION TEST

Methods

The studies used a black:white test box procedure as described below. Male albino (BKW) mice were used, initially weighing 25-30 g. In their home cage, mice were housed in groups of 10 and given free access to food and water. The mice were kept on a 12 hour light and 12 hour dark cycle with lights off at 8:00 a.m. and on at 8:00 p.m.

The test box consisted of an open-topped box (45×27×27 cm), 40% of the area painted black and illuminated with a dim red light (1×60 W), the other painted white and brightly illuminated with white light (1×60W) located 17 cm above the box. Access between the two areas was enabled by means of a 7.5×7.5 cm opening located at floor level in the center of the partition (which also served to prevent diffusion of light between the two compartments of the test box). The floor area was lined into 9 cm squares.

The habituation test was carried out daily by placing mice in the center of the white section of the test box (mice taken from dark home environment in a dark container, to the experimental room maintained in low red lighting, and would normally be averse to the bright white conditions). Testing was carried out between 8:30 and 12:30 p.m. The test period was 5 minutes per day. Behavior was assessed via remote video recording, and the following measures taken:

1. Latency to move from the white to the black section (sec).
2. Numbers of exploratory rears in the white and black sections during the 5 minute test.
3. Numbers of line crossings (exploratory locomotion) in the white and black sections during the 5 minute test.
4. Time spent in the black section of the box during the 5 minute test.
5. Numbers of transitions between the black and white sections of the test box during the 5 minute test (since this parameter was not changed in any situation in the present studies, data for transitions is not given or commented on further).

Generally, as animals habituated to the test system, they would move into the black section of the box where behavioral exploration was exhibited as exploratory rears and line crossings.

Scopolamine was used at a dose of 0.25 mg/kg i.p. to disrupt habituation patterns. This could be achieved by a single acute challenge with scopolamine which disrupted the learning patterns on the day of treatment, with subsequent recovery, or by continued daily treatment with scopolamine 1 hour before test. The dose of scopolamine was carefully selected as one which did not cause autonomic disturbance (0.25 mg/kg i.p. methyl scopolamine failed to influence behavior). Under the influence of 0.25 mg/kg i.p. scopolamine mice would go to the door in the partition, investigate the opening and pass the head or body through, but without association of the dark environment with escape from the brightly-lit averse environment.

Results

The normal learning curve for mice in the habituation test was 5-6 days as evidenced by reduced rearings and line crossings in the white compartment, increased in the black, reduced latency to move to the black and increased % of time spent in the black. Acutely administered scopolamine causes impairment in control animals. Example data is given here for rears: mice had 'learned' to avoid the white averse environment and by day 6 were carrying out most of their behavior in the black—this was prevented by scopolamine which caused an impairment characterized by increased activity in the white, decreased in the black. This impairment caused by scopolamine can be prevented by arecoline. The selection of dose and route for arecoline are critical to avoid unwanted autonomic disturbance. The arecoline is given continuously by intraperitoneal infusion from Alzet osmotic minipumps at a dose of 50 mg/kg/day. It is interesting that while the continuous treatment with this dose of arecoline inhibited the scopolamine impairment of habituation, the time course of the basic 'learning' or habituation was unaffected by the presence of arecoline. This contrasts with findings for the ACE inhibitor SQ 29,582.

Using the same procedure as described above, control mice and mice treated with SQ29,852 were subject to the habituation procedure and challenged with scopolamine on days 6 and 10. Firstly, it was seen that the basal learning procedure was speeded by treatment with SQ29,852 at doses as low as 0.0005mg/kg b.d. Secondly, the treatments with SQ29,852 were shown to completely antagonize the impairments caused by scopolamine. SQ29,852 doses were lowered on days 7-10 to 0.00005mg/kg i.p. b.d.: this is because an anxiolytic potential was becoming apparent using the twice daily, continuous treatment regime.

Assessments of the potential of hydergine to improve cognitive function in the mouse habituation test utilized the same test protocol as described so far for arecoline and the ACE inhibitor. Hydergine was obtained as a proprietary product and the human dose titrated to mouse for single daily challenge, orally, 60 minutes before test. Treatment with hydergine was clearly shown to enhance 'learning' in the mouse habituation test. Rearing in the white section rapidly diminished as this behavior correspondingly increased in the black, and crossings in the white decreased significantly below control values by day 2 of testing, again with corresponding increases in the black and increased % of time in the black was significant on day 2 as were the reductions in latencies to move from the white to the black section on days 2, 3 and 4 of testing.

The treatment with hydergine was not associated with any anxiolytic potential and the dose regime was maintained constant at 0.1 mg/kg p.o. daily. After 4 days some motor impairment and sedation developed in a small proportion of animals; this particularly influenced the latency to move from the white environment and data for such animals had to be excluded from analyses.

A very important observation was that while hydergine (like the ACE inhibitor but in contrast to arecoline) could enhance basal learning, it was not able to antagonize the influence of scopolamine to impair performance whether measured as changed rearing, changed line crossings or changed % time in black, and latency to move out of the white, aversive environment. This failure to antagonize, indeed, to any way influence the impairment caused by scopolamine contrasts with the marked antagonistic effects of arecoline and the ACE inhibitor SQ29,852.

In a further series of experiments mice were allowed to habituate for 10 days and then were challenged daily with scopolamine, 0.25mg/kg. The habituation was impaired throughout-the time of scopolamine challenge. If, after impairment with scopolamine was established, mice were given arecoline (50mg/kg/day by intraperitoneal infusion from Alzet osmotic minipumps), or SQ29,852 (0.5 µg/kg i.p. b.d.) daily with the scopolamine treatment, then the scopolamine impairment was completely prevented.

b) ABILITY TO IMPROVE BASIC PERFORMANCE AND TO ANTAGONIZE A SCOPOLAMINE IMPAIRMENT IN A FOOD REINFORCED ALTERNATION TASK IN THE RAT USING AN ELEVATED T MAZE

Methods

The studies used male Lister hooded rats initially weighing 300–350 g. Rats were normally housed in groups of 5 in a room maintained at 22°±1° C., on a 12 hour light:dark cycle with lights on at 8:00 a.m. and off at 8:00 p.m. The test room was maintained under identical conditions, and was sound-proofed.

The apparatus and technique used was essentially that of Salamone et al. (Behav. Brain Res. 13, 63–70, 1984) using a T maze constructed of wood and elevated 30 cm from the ground with side arms measuring 60 cm×10 cm and start arm measuring 80 cm×10 cm. A small metal cup was placed towards the end of each side arm; these held the reward pellets as appropriate. A line was marked 20 cm from the start of each side arm.

Animals were food deprived excepting for 1 hour post-test, for 2 days prior to testing and throughout the 9 day test period, but water was available 'ad libitum'. Animals maintained 85% of normal body weight throughout testing. A few banana-flavored reward pellets were mixed with the food to habituate the rats to the taste of the pellets. Our rats showed clear preference for banana-flavored pellets as compared with their normal laboratory chow.

Rats were allowed 10 minutes habituation to the T maze on day 1 (both arms baited with banana-flavored reward pellets, 4×45 mg pellets in each cup) and were subject to a pretraining period of reinforced alternation on days 2–5 of test, with training on days 6–9. All training consisted of paired trials (each pair constituting a 'run'), the first being 'forced' in that one arm was blocked with a wooden barrier while the other was baited (for a positive response on the forced trial the rat must take the food). The second was a 'choice' trial in which reward pellets were placed in the arm opposite to that reinforced on the first trial of the pair. A correct choice was when the rat entered the arm containing the food on the choice trial, crossing the point marked 20 cm from the start of the side arm.

In addition, to correct/incorrect choice, latency to reward was recorded for both forced and choice trials. 4 runs/day were carried out on pretraining days (inter-trial interval 9 sec, inter-run interval 30 sec), 6 runs/day during training (inter-trial interval 30 sec, inter-run interval 60 sec).

6 groups of animals (n=7 per group) were used as follows:
1. Control group—saline 1 ml/kg i.p. b.d.
2. Scopolamine group—scopolamine 0.25 mg/kg i.p. b.d.
3. Arecoline group—arecoline 30 mg/kg/day by intraperitoneal infusion from an Alzet osmotic minipump (carefully selected as maximum dose tolerated).
4. SQ29,852 group—SQ29,852 1.0 mg/kg i.p. b.d.
5. Scopolamine +arecoline group.
6. Scopolamine +SQ29,852 group.

Results

Scopolamine was shown to impair performance in the food reinforced alternation task using an elevated T maze. This impairment was seen as delayed forced latencies, delayed choice latencies and reduced % correct responses. This impairment was evident both during the pretraining days (2–5) and training days (6–9). At no time was arecoline or SQ29,852 treatment shown to enhance basal performance in the T maze task. However, arecoline and SQ29,852 were shown to antagonize the effects of scopolamine on days 2–5. The antagonism afforded by SQ29,852 was less marked during days 6–9: that afforded by arecoline was more consistent.

Using the same strain of rats and the same doses of SQ29,852 (1.0 mg/kg i.p.) assessment of anxiolytic action was carried out using an upscaled version of the black:white test box suitable for rat testing. Both compounds showed an anxiolytic profile and it is considered that this activity may have seriously interfered with responding on the T maze. Thus, while animals were challenged by a novel task on the first few days of training, this novelty was not apparent as learning progressed, and rats were noted to be 'nonchalant' to the test situation. However, the data obtained with SQ29,852 shows that a scopolamine impairment in a food reinforced alternation task in the rat using an elevated T maze can be antagonized by SQ29,852.

c) ABILITY TO IMPROVE DISCRIMINATIVE AND REVERSE LEARNING IN THE MARMOSET USING THE WISCONSIN GENERAL TEST APPARATUS

Methods

The studies used male and female marmosets aged 15–18 months (300–340 g) which had been bred at University of Bradford, England, or bought as weanlings, and had been regularly handled. All experiments were carried out by one experimenter since, while it is possible for two experimenters to work together for double-blind dosing of animals, the relationship built between the experiment/marmoset makes it impossible to design the experiments for double-blind use of marmosets. Marmosets used in the present studies were coded 081, J59 and 025.

Shaping discrimination learning and training

The procedures followed for shaping and reverse learning were standard and would be applied to any marmoset when using the WGTA.

i) Shaping and discrimination learning

The animal is first presented with open, baited food wells and the stimuli are gradually moved over the wells on successive trials until they are completely covered. When the animal will respond to both stimuli (both are rewarded at this stage) and at both food wells, shaping is complete and discrimination learning, where the reward is always put under one and the same stimulus, can begin. For stimuli one can use small toy figures or 'junk' objects about 5 cm in the largest dimension (junk objects are pen-tops, bottle tops, etc.). Animals 081, J59 and 025 were generally nervous of the small toy figures presented to them (e.g. farm animals, cowboys and Indians) and so the discriminative learning used a rubber bung (positive) and syringe needle cap (negative). Animals may meet different objects during its experimental career. However, a marmoset within our limited experience (and in the wider experience of others, Baker and Ridley) never forgets the first shaping and discriminative learning trials, and the first objects used, the rubber bung and needle cap for the marmosets used in the present studies, can be used to help animals when they are later given very complex tasks, and lose confidence.

In order to ensure that the animal learns the discrimination on the basis of the stimulus association rather than because the reward is always on, say, the left, the left/right position of the stimuli is varied according to a "pseudo-random" schedule. In one such schedule, described by Gellerman (1933; J. Genet. Psychol. 42, 206–208), the reward appears unpredictably on the left or right, though in each block of 10 trials it appears 5 times on each side. This schedule was used in the present experiment. Marmosets are easily distracted by visual as well as auditory interference. The test cage therefore has opaque walls on all sides and a smoked Perspex panel facing the shutter. Sawdust should not be used on the floor of the cage otherwise the animal may spend a considerable time sifting through it.

It was not necessary to maintain food deprivation during these training sessions. The procedure was to feed the animal its normal daily diet after the day's training session (sessions generally restricted to 8:30–11:30 a.m. and 12:00–3:00 p.m., feeding at 4:00 p.m.).

ii) Training on the Gellerman Schedule

Animals are tested usually on 4 or 5 consecutive days to gain 90/100 correct choices. They are then allowed a 1 week break before confirming a criterion of 18/20, and the 9/10. It is important that the experimenter knows the animals, and never makes them 'work' until bored or fail to concentrate. For 081, J59 and 025 the critical challenge was either 40 trials/days or 15 minutes of trials.

To prevent 'boredom' weekend breaks appeared very important and therefore generally experiments are carried out over a maximum 5 days. However, since there appeared to be a delay in onset of the action of SQ29,852, the test time was extended to 8 days.

SQ29,852 was prepared in normal saline and was given twice daily (close to 7:00 a.m. and 7:00 p.m. for animals tested 12:00–3:00 p.m., 8:00 a.m. and 8:00 pm. for animals tested 8:30–11:30 a.m., but always 60 minutes before test).

iii) Reverse training

Objects used for the reverse training remained constant at yellow flask top/red pen top. Objects were presented until six correct consecutive trials were recorded, and the number of attempts before the 6 correct trials noted. Positive objects (with food reward) were alternated. For example, day 1 red pen top was first positive object, after 6 consecutive selections of the red pen top, the yellow flask top became the positive object, and was presented until it was selected on 6 consecutive attempts. The last positive object of each day (yellow flask top in this case) would be the first positive object of the following day.

On each day of testing, marmosets were subjected to a reverse learning task immediately after the discriminative task. For example, the objects used were yellow flask top/red pen top. If the yellow flask top was the last positive object of the previous day, it would be the first positive object of the test day and a marmoset would be expected to discriminate this from the red pen top by selecting the yellow flask top on 6 consecutive attempts. The number of attempts before this criterion was reached was determined on each day and the mean numbers of days 1–4 (vehicle), 5–8 (vehicle or SQ29,852) and 9–12 (vehicle or SQ29,852) are given (termed D for first discriminative task). Marmosets were then subject to a reverse learning task, i.e., on completion of the 6 correct selections of the yellow flask top, the marmoset would be required to reverse to selecting the red pen top on 6 consecutive occasions (this now being the positive, food rewarded object). The mean number of attempts made in this reverse situation was determined for days 1–4, 5–8 and 9–12 as above, and indicated R.

Results

During the first 4 days of the trials the three marmosets found reverse training more difficult than the initial discriminative learning (approximately 9 trials to criterion on discriminative learning, D, and 12 to criterion on reverse learning, R). Animal 081 was maintained on vehicle and he maintained responding on discriminative learning, continuing to find reverse learning difficult (on days 9–12 10 trials to criterion on discriminative learning but 18 on reverse learning).

The performance of animal J59 improved gradually over 8 days of treatment with SQ29,852, 0.1 mg/kg s.c. b.d. ($11>9>7$ for discriminative learning, $13>9>7$ for reverse learning), while animal 025 failed to improve during the first 4 days of treatment, but did improve over the subsequent 4 day period ($8>5$ for discriminative learning, $12>9$ for reverse learning).

These experiments were carried out double blind. However, the experimenter made full comments on the quality of behavior of these 3 marmosets during testing, all of which were well known in terms of their normal behavioral repertoire in the Wisconsin test. During treatment with SQ29,852, the comment was consistently made that the animals appeared "too carefree to work". The dose of SQ29,852 used is markedly anxiolytic in the marmoset, and it is our experience that animals fail to work well when undergoing full anxiolysis. Nevertheless, the size of improvement seen in J59 and 025 was important in that these animals have shown constant responding over many months. It is clear that SQ29,852 is able to improve performance in both discriminative and reverse learning tasks in the marmoset.

CONCLUSIONS

Assessment of Ability to Improve Cognition and Cognitive Impairment a) A mouse habituation test was used in which mice were repeatedly placed in the white compartment of a white:black test box. On repeated exposure to the test situation, mice 'learn' to avoid the averse white, brightly-lit environment and move rapidly into the black where they spend a larger proportion of time and show most exploratory rearings and line crossings.

The habituation (learning) time is 5–6 days. This basic 'learning' time was not influenced by arecoline (50 mg/kg/day given by continuous intraperitoneal infusion: dose and route selected to avoid unwanted autonomic effects). However, this dose of arecoline successfully antagonised an impairment in habituation caused by acute challenge with scopolamine (0.25 mg/kg i.p., dose again carefully selected to avoid excessive peripheral autonomic disturbance, and particularly to avoid influence on vision which can influence performance in the test: lack of effect on vision was established by visual observation and by measurement of pupil function). Methyl scopolamine at a dose of 0.25 mg/kg i.p. failed to influence mouse habituation. The effect of scopolamine was marked: animals which had learned to avoid the white environment failed to enter the black, excepting for short periods of time, even though they easily found the door, and thus the rapid exit into the black and avoidance of the white environment was prevented by scopolamine treatment.

In contrast to arecoline, the speed of habituation was enhanced by treatment with low doses of SQ29,852 (0.0005 mg/kg i.p. b.d.). Anxiolytic potential, which influenced the test procedure, generally developed on longer term treatment with these doses of the ACE inhibitor, and doses for use in the habituation test were subsequently lowered. SQ29,852 was found to antagonize the impairment in habituation performance caused by acute challenge with scopolamine. The dose which was fully effective against scopolamine was 0.0005 mg/kg i.p. b.d. SQ29,852.

Hydergine (0.1 mg/kg p.o. once daily) was shown to speed the habituation process in a similar manner to the SQ29,852 ACE inhibitor (both in contrast to the failure of arecoline), but hydergine treatment failed to influence the impairment in habituation caused by acute challenge with scopolamine (which contrasts with the actions of both the SQ29,852 ACE inhibitor and the cholinomimetic agent).

Further studies allowed habituation to progress for 10 days before continuous impairment by scopolamine given daily for up to 14 days. This persistent impairment caused by scopolamine could be antagonized by arecoline (50 mg/kg/day by intraperitoneal infusion) and by SQ29,852 (0.5 µg/kg i.p. b.d.).

b) In a food reinforced alternation task in the rat using an elevated T maze arecoline (30 mg/kg/day by intraperitoneal infusion) and SQ29,852 (1.0 mg/kg i.p. b.d.) were shown to antagonize an impairment caused by scopolamine. This antagonism was particularly marked on pretraining days 2–5, but was less marked on training days 6–9. This may reflect the fact that the test becomes less challenging for the rats as training progresses, and that SQ29,852 is anxiolytic at the dose used. Thus, it was observed that rats became increasingly 'nonchalant' about working on the test paradigm. Whatever, the data obtained with arecoline and SQ29,852 clearly indicates that a scopolamine impairment in learning in a rat test can be improved both by a cholinomimetic and SQ29,852.

c) Marmosets were trained in a Wisconsin General Test Apparatus to discriminate between food rewarded and non-rewarded objects. After shaping to a criterion of 90/100, 18/20 and 9/10 correct reponses (the 9/10 being repeated on several days), objects were changed and marmosets expected to select a new positive object on 6 consecutive occasions (discriminative learning), and then to change to selecting the second object (now positive in terms of food reward) on 6 consecutive occasions (reverse learning). Marmosets used had shown constant responding over many months and there had been no improvement in either discriminative or reverse learning. However, after 8 days of treatment with 0.1 mg/kg s.c. b.d. SQ29,852 marmosets showed clear improvement in both discriminative and reverse learning. The onset of action appeared to be delayed for some 4 days. It was also considered that the anxiolytic action of SQ29,852 would interfere with testing, making the animals less inclined to work. However, it is clear that SQ29,852 is capable of improving performance in established learning tasks in the common marmoset.

EXAMPLE 8

The following experiments were carried out to demonstrate the effectiveness of the ACE inhibitor SQ29,852 in inhibiting loss of cognitive functions.

Adult male Sprauge-Dawley rats (Charles River, Wilmington, MA), age 25 weeks and weighing 350–400 g, were separately housed in stainless steel cages with continuous access to food and water, a 12-hour lightdark cycle, and constant room temperature of 22° to 24° C. All testing took place approximately 6 hours into the dark component of the light-dark cycle and was conducted in a dimly lighted soundproof room using a standard shuttle box device (Lehigh Valley Electronics #146-04), a plexiglass chamber (50×20×20 cm) divided by a center barrier 7 cm in height. The conditioned stimulus consisted of a 10-second tone provided by a Sonlert mounted in the midpoint of the ceiling of the chamber. Floor current of 0.8 mA was delivered by a constant current shocker-scrambler (Lehigh Valley Electronics #133-33).

The day before the initiation of training each animal was allowed to explore the experimental chamber for 10 minutes without any tone or shock. Training was conducted for 15 days following the day of experimental chamber exploration. Each animal received 20 trials per day on a 30-second variable interval schedule. No drug treatment was administered during the training period. Shock could be avoided by shuttling from one side of the center barrier to the other during the 10-second tone period. If an animal did not cross the center barrier during this period, the tone remained on and the floor shock was delivered until the animal escaped to the other half of the chamber. Animals which consistently remained on the center barrier were removed from the study. Automatic counters recorded the number of avoidance responses, escapes, and intertrial crossings, while a running time meter recorded the total shock duration for each animal.

Animals not meeting the admittance criterion of correct avoidance responding on at least 85% of the trials for 4 out of the last 5 days of training were removed from the study. A total of 36 rats reaching the admittance criterion were tested for extinction of conditioned avoidance response (CAE) during 14 days. They were randomly assigned to SQ29,852 (1 mg/kg, 10 mg/kg and 30 mg/kg) and saline control, with each test group at each dosage comprising 9 rats. All solutions were prepared fresh and administered i.p. (1 mg/ml volume) on the 2 days prior to testing and then 1 hour before it. Testing consisted of 20 trials per day identical to those previously described, except that no shock was administered if an animal failed to shuttle during the 10-second tone period. The tone was simply discontinued and the testing proceeded.

Two-way analysis of variance of the CAE data yielded an overall significant difference in the rate of shuttle extinction between treatment groups.

The present findings as seen from the accompanying Figure indicate that the ACE inhibitor, SQ29,852, possesses protective effects on memory of previously learned tasks while the saline control which does not have ACE inhibiting activity does not have protective effects against loss of memory of previously learned tasks.

It will also be appreciated that all of the above compounds and formulations may be employed in treating or delaying progression of Alzheimer's disease.

EXAMPLE 9

The following experiments were carried out to demonstrate the ability of captopril and SQ 29,852 to improve mouse habituation performance during continuous scopolamine administration or following lesions of the nucleus basalis.

Methods

The studies used the habituation procedure described in Example 7. Young adult male mice, 25–30 g, were used. However, habituation patterns were persistently disturbed using three approaches:

1. Continuous administration of scopolamine 0.25 mg/kg i.p. b.d.
2. Electrolesions of the nucleus basalis of Meynert.
3. Ibotenic acid lesions of the nucleus basalis of Meynert.

Lesions of the nucleus basalis were induced using standard stereotaxic surgery (Kopf stereotaxic instrument, chloral hydrate anaesthesia, 150 mg/kg s.c.) for the location of injection units at Ant. 2.3 mm (relative to the zero of the Kopf frame), Vert. 4.5 mm (below the skull surface) and Lat. ±2.4 min (from the skull midline). Ibotenic acid lesions were produced by the nucleus basalis in a volume of 0.25 $\mu$l (prepared in phosphate buffer). The injection unit was allowed to remain in place for 4 minutes. Electrolesions of the nucleus basalis were induced by use of an electrode measuring 0.3 mm diameter, insulated except at the tip, and passing a current of 1 mA for 10 sec. Animals subject to-lesion of the nucleus basalis were used in the habituation test after 2–3 days of recovery. At the end of the experiment mice were killed for determination of levels of ChAT in the septum, frontal cortex, hippocampus and striatum. The radioenxymatic technique used to determine ChAT levels was that of Fonnum (J. Neurochem., 24, 407–409, 1975) with a modified incubation period of 10 minutes. Both the ibotenic acid lesions and the electrolesions of the nucleus basalis were shown to reduce ChAT activity in the frontal cortex (by 38–49%) without influence on ChAT activity in the hippocampus or striatum.

Mice receiving continuous scopolamine treatment or which had been subject to ibotenic acid lesions or electrolesions of the nucleus basalis were subject to habituation testing without drug treatment, with vehicle treatment, or with continuous treatment with captopril 0.05 mg/kg i.p. b.d. or scopolamine (0.0005 mg/kg i.p. b.d.).

Results

Mice given continuous treatment with scopolamine failed to habituate to the black:white test box over a 8-day period. During this time the mice distributed their behavior approximately 50% between the white and black sections of the box (seen as rears/5 min on FIG. 2, as crossing/5 min on FIG. 3, as % time in black and latency to move from the white to the black on FIG. 4). In contrast to this data, mice which received continuous treatment with captopril (0.05 mg/kg i.p.) or SQ29,852 (0.0005 mg/kg i.p. b.d.) showed clear habituation patterns, at least equal to those exhibited by young adult mice which had not received any treatment. Thus, on the 3rd-8th days of habituation, mice treated with captopril or SQ 29,852 had 'learned' to avoid the more aversive white environment and had distributed behavior in preference of the black (see for rears/5 min on FIG. 2 crossings/5 min on FIG. 3, % time in black and latency to move from the white to the black on FIG. 4). The effects of the ACE inhibitors on latency to move to the preferred black environment was most dramatic in that mice given continuous scopolamine treatment took some 19–23 sec to move to the black environment: under the influence of continued captopril treatment this was reduced progressively to values of 2–3 sec, whilst under the influence of SQ29,852 treatment movement from the white was immediate (faster than time taken to operate remote video recording) to 3 sec. It is also noticeable that under the influence of the ACE inhibitors the time taken for movement from the white was initially in the range recorded for normal mice (10–12 sec, compared to the approximate 20 sec recorded for the scopolamine treated mice).

Lesions of the nucleus basalis disturbed habituation profiles even more profoundly than continuous scopolamine treatment. Thus, the lesioned mice failed to associate the black with escape from the aversive white environment and exhibited more behavior in the white than the black section of the box (seen for rears/5 min on FIGS. 5 and 8, crossings/5 min on FIGS. 6 and 9, % time in black and latency to move from the white to the black on FIGS. 7 and 10, figures quoted for electrolesions and ibotenic acid lesions respectively.) At no time during a 8-day test period did the nucleus basalis lesioned mice show habituation to the test situation. However, whether lesions had been induced by electrocoagulation or by ibotenic acid, nucleus basalis lesioned mice given continuous cover with the ACE inhibitors captopril or SQ29,852 habituated to the black:white test box situation. Significant differences between the behavior of the non-treated and treated mice were seen from the first day of treatment, and distribution of behavior between the black and the white sections occurred correctly over a 4-day period such that by day 4+ mice were spending more time in the black compartment (see FIGS. 5 and 8 for rearing, 6 and 9 for crossings, 7 and 10 for % time in black and latency to move to the black). Again, the most dramatic changes were seen on the measure of latency to move from the white to the black environment. Following electrolesions of the nucleus basalis this latency was delayed by some 18-23 sec. On continued treatment with captopril or SQ29,852 latency was reduced on the first day of test to 10-12 sec, and was then progressively reduced as mice habituated to the test system such that movement to the black was immediate, or within 3 sec (FIG. 7). After ibotenic acid lesions of the nucleus basalis latency was again delayed in the order of 20 sec, although the detriments-were not as marked on days 1 and 2. However, whilst the lesioned mice failed to habituate, those which received the ACE inhibitors learned progressively to avoid the white environment, and again, movements were immediate or within 3 sec (FIG. 10).

Figure 2:
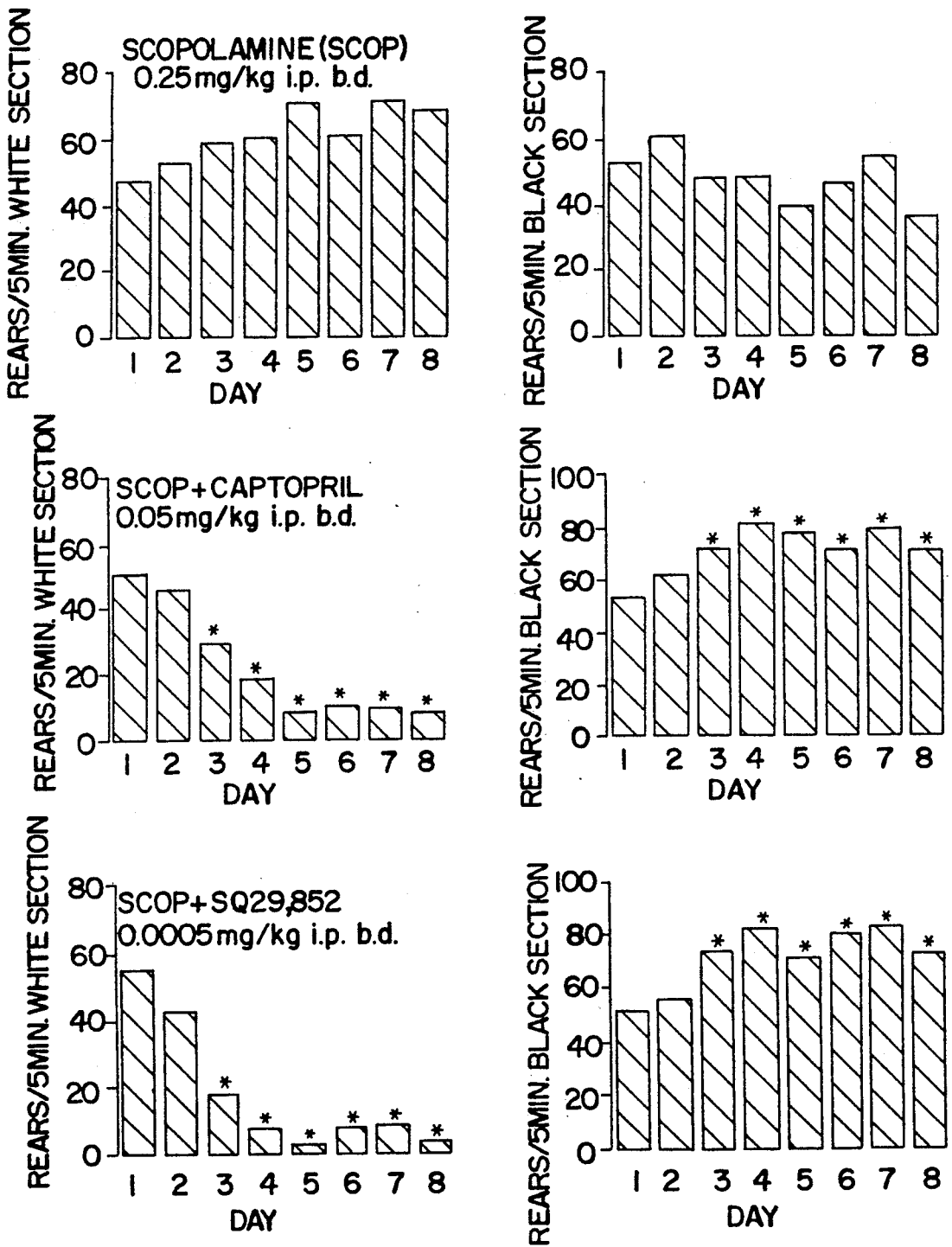
Figure 5:
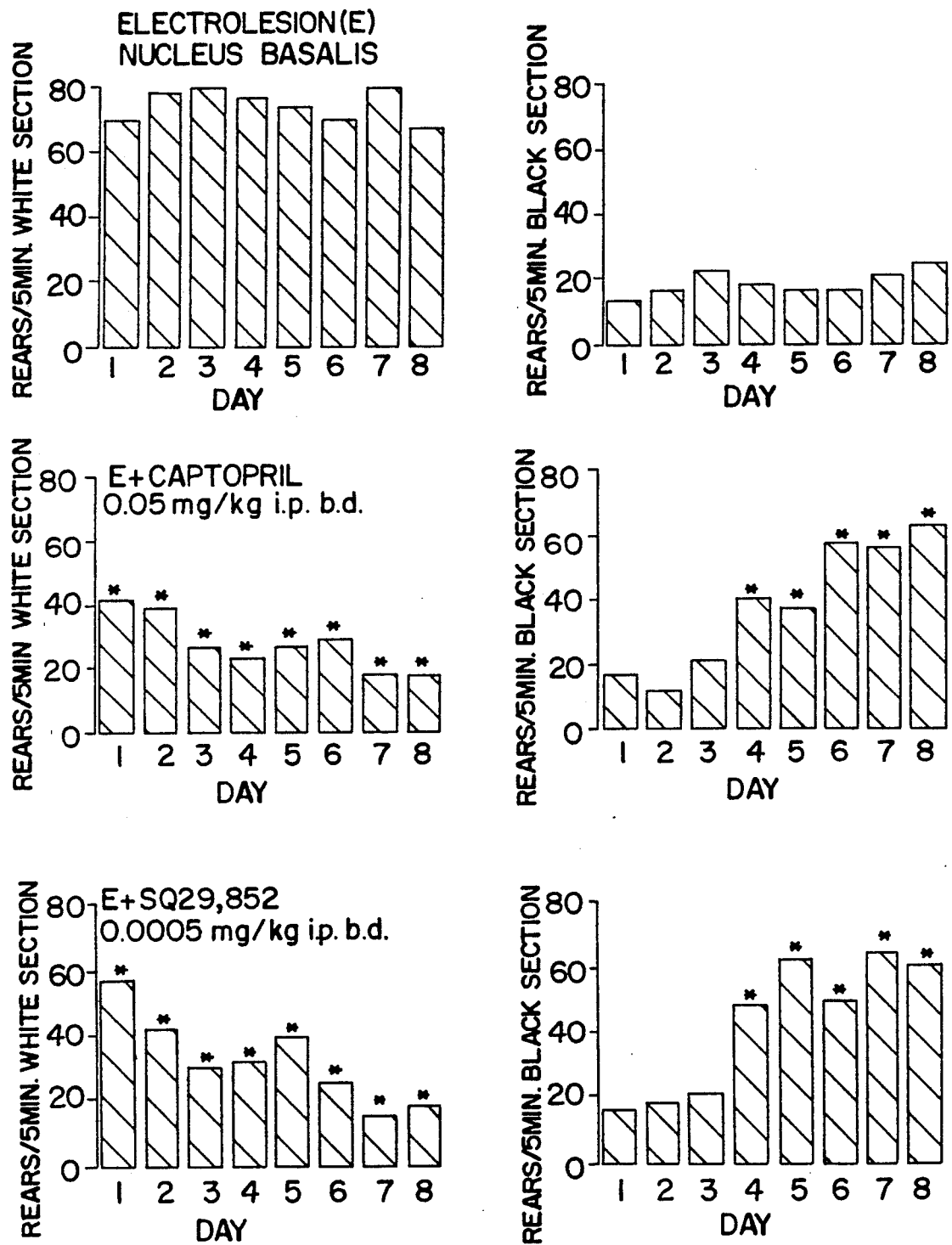
Figure 6:
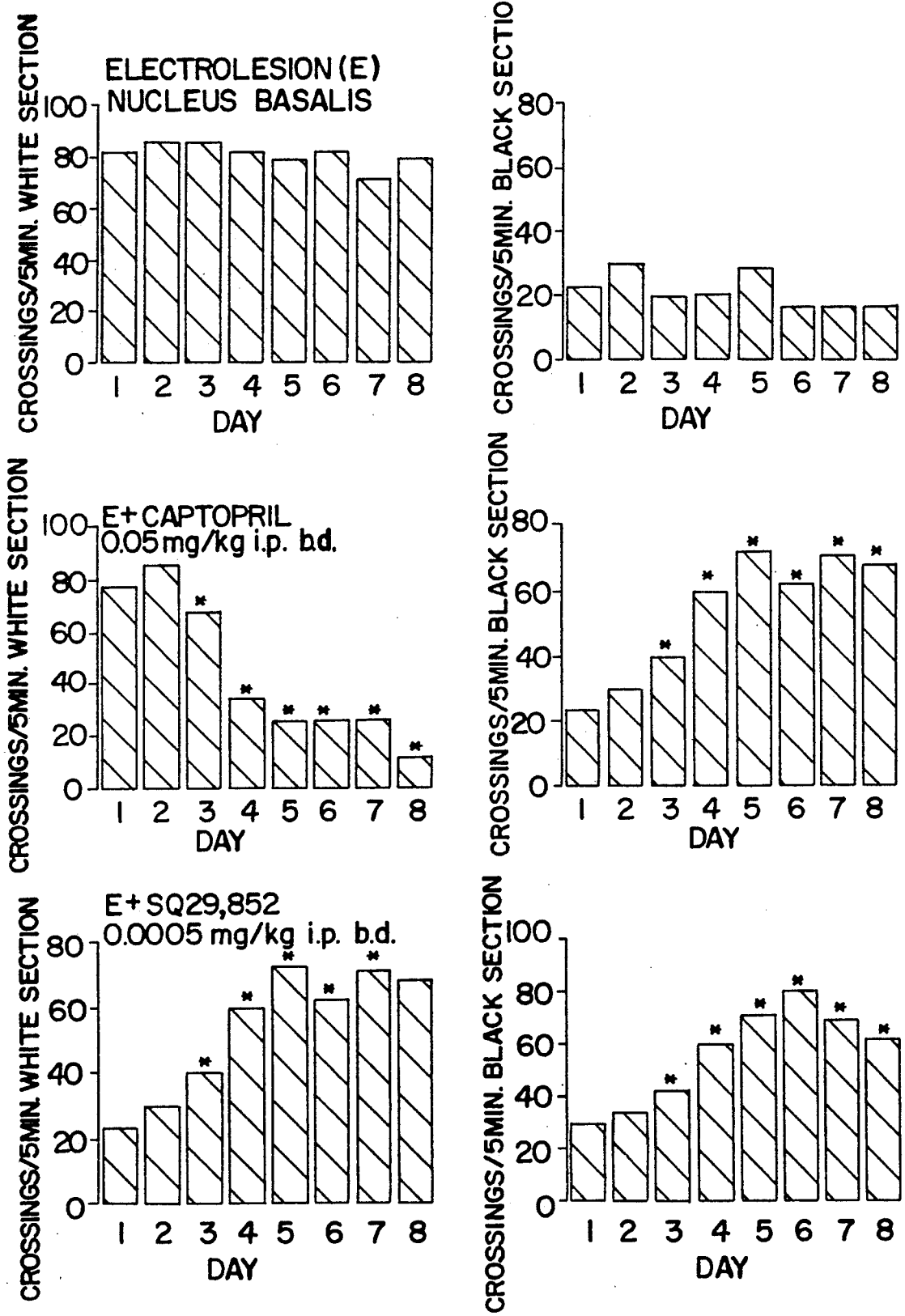
Figure 8:
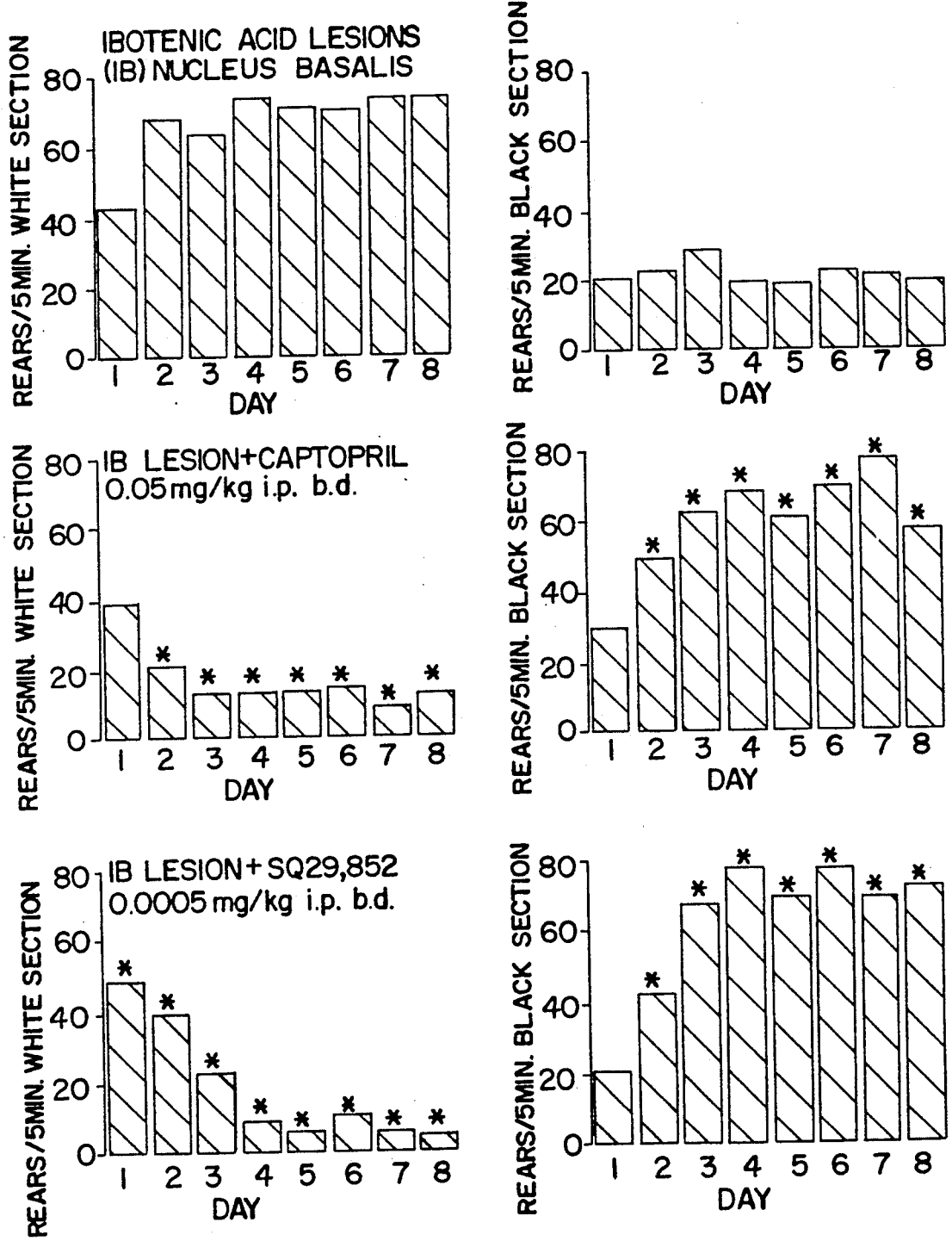
Figure 9:
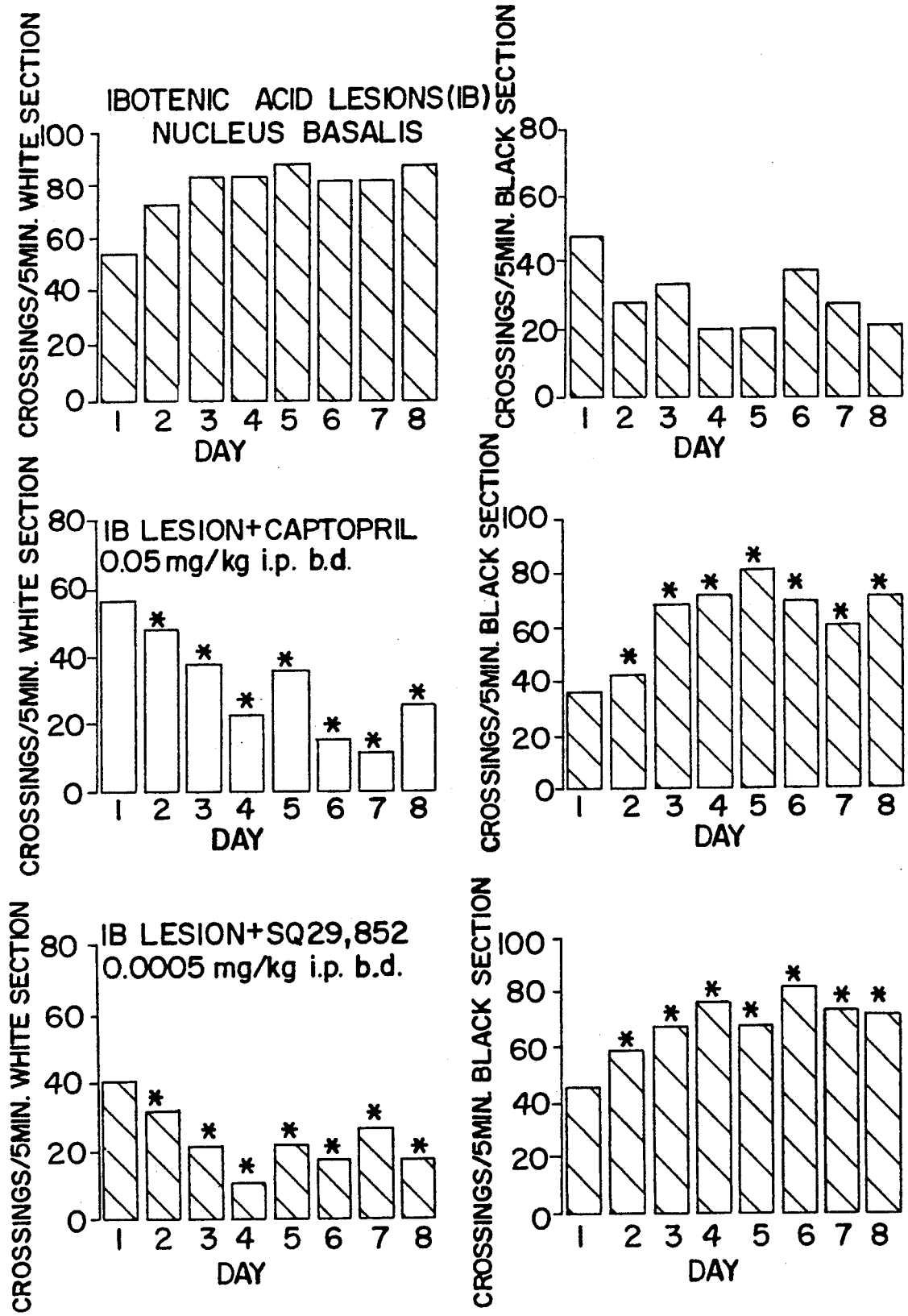

In referring to FIGS. 2 to 10, in FIG. 2, n(number of mice)=5, S.E.M.s<11.3-13.0%, *P<0.001 (enhanced habituation), in FIG. 3, n=5, S.E.M.s<7.6-11.9%, *P<0.01-P<0.001 (enhanced habituation), in FIG. 4, n=5, S.E.M.s<10.1-13.6%, *P<0.05-P<0.001 (enhanced habituation), in FIG. 5, n=5, S.E.M.s <10.3-12.9%, *P<0.01-P<0.001 (enhanced habituation), in FIG. 6, n=5, S.E.M.s<8.6-11.0%, *P<0.001 (enhanced habituation), in FIG. 7, n=5, S.E.M.s<9.4-12.8%, *P<0.05-P<0.001 (enhanced habituation), in FIG. 8, n=5, S.E.M.s<11.0-12.9%, *P<0.001 (enhanced habituation), in FIG. 9, n=5, S.E.M.s<10.3-13.1%, *P<0.001 (enhanced habituation), in FIG. 10, n=5, S.E.M.s<8.7-13.0%, *P<0.001 (enhanced habituation).

Conclusions

Habituation performance of mice is impaired by continuous scopolamine treatment or by lesions of the nucleus basalis. Such mice fail to learn to avoid the aversive white environment of a black:white box. However, when such mice are given continued treatment with the ACE inhibitors captopril or SQ29,852 they are then able to habituate to the test in a manner similar to that of normal mice. Thus, the cognitive deficits caused by continued scopolamine treatment or destruction of the cell bodies supplying cortical and limbic acetylcholine (but with major deficits in the cortex) can be inhibited by the ACE inhibitors captopril or SQ29,852. Both test protocols would be considered relevant to the impairments seen in central acetylcholine function in Alzheimer's disease. Thus, in addition to improvements in the performance of aged animals, further evidence is presented here that the ACE inhibitors may also be valuable in treating cognitive deficits of the Alzheimer's type.

It is also seen that SQ29,852 at a dosage of 1/100th of that of captopril was essentially equivalent in performance to captopril in the above test so that SQ29,852 is 100 fold as potent as captopril in the above test.

EXAMPLE 10

The following experiments were carried out to demonstrate the influence on basal performance and scopolamine deficits in a food reinforced alternation task in the rat using an elevated T-maze: influence on aged performance.

Methods

Studies on young animals used male Lister hooded rats initially weighing 300-350 g (11-15 weeks). Studies on aged animals used female Lister hooded rats initially weighing 400-425 g (13 months). Rats were normally housed in groups of 5 in a room maintained at 22°±1° C., on a 12 hour light:dark cycle with lights on at 8:00 am and off at 8:00 pm. The test room was maintained under identical conditions and was sound proofed.

The apparatus and technique used was essentially that of Salamone et al (Behav. Brain Res. 13, 63-70, 1984) using a T-maze constructed of wood and elevated 30 cm from the ground with side arms measuring 60 cm×10 cm and start arm measuring 80 cm×10 cm. A small metal cup was placed towards the end of each side arm; these held the reward pellets as appropriate. A line was marked 20 cm from the start of each side arm.

Animals were food deprived excepting for 1 hour post-test, for 2 days prior to testing and throughout the 9 day test period, but water was available 'ad libitum'. Animals maintained 85% of normal body weight throughout testing. A few banana-flavored reward pellets were mixed with the food to habituate the rats to the taste of the pellets. Our rats showed clear preference for banana-flavored pellets as compared with their normal laboratory chow.

Rats were allowed 10 minutes habituation to the T-maze on day 1 (both arms baited with banana-flavored pellets, 4×45 mg pellets in each cup) and were subject to a pretraining period of reinforced alternation on days 2-5 of test, with training on days 6-9. All training consisted of paired trials (each pair constituting a 'run'), the first being 'forced' in that one arm was blocked with a wooden barrier whilst the other was baited (for a positive response on the forced trial the rats must take the food). The second was a 'choice' trial in which reward pellets were placed in the arm opposite to that reinforced on the first trial of the pair. A correct choice was when the rat entered the arm containing the food on the choice trial, crossing the point marked 20 cm from the start of the side arm.

In addition to correct/incorrect choice, latency to reward was recorded for both forced and choice trials. 4 runs/day were carried out on pretraining days (inter-trial interval 0 sec, inter-run interval 30 sec), 6 runs/day during training (inter-trial interval 30 sec, inter-run interval 60 sec).

In young animals, the detrimental effect of scopolamine and the antagonism of this by SQ 29,852 was confirmed using 4 groups of animals (n=7 per group):

1. Control group—saline 1 ml/mg i.p. b.d.
2. Scopolamine group—scopolamine 0.25 mg/kg i.p. b.d.
3. Scopolamine+SQ 0.05 group—SQ29,852 0.05 mg/kg i.p. b.d. given at the same time as scopolamine.
4. Scopolamine+SQ 0.005 group—SQ29,852 0.005 mg/kg i.p. b.d. given at the same time as scopolamine.

In the studies using aged animals 6 groups of rats were used:

| Group Name | Treatment | n |
| --- | --- | --- |
| Young adults (vehicle) | Female HL rats age 11-15 weeks & 1 ml/kg saline i.p. b.d. | 5 |
| Old age rats (Vehicle) | Female HL rats age 13 months & 1 ml/kg saline i.p. b.d. | 4 |
| Old age & SQ 0.005 | Female HL rats age 13 months & 0.005 mg/kg SQ29,852 i.p. b.d. | 6 |
| Old age & SQ 0.0005 | Female HL rats age 13 months | 6 |

-continued

| Group Name | Treatment | n |
|---|---|---|
| | & 0.0005 mg/kg SQ29,852 i.p. b.d. | |
| Old age & CAPT 0.05 | Female HL rats age 13 months 0.05 mg/kg captopril i.p. b.d. | 6 |
| Old age & CAPT 0.025 | Female HL rats age 13 months 0.025 mg/kg captopril i.p. b.d. | 6 |

In a further series of experiments impairments in T-maze performance were induced by the injection of hemicholinium-3 into the lateral ventricle. Rats were subject to standard stereotaxic surgery for the implantation of chronically indwelling guides for subsequent injection (14 day recovery) into the ventricular system. Rats were then tested as described above. Preliminary experiments assessed the potential of SQ29,852, 0.005 mg/kg i.p. b.d., to antagonize the impairments caused by hemicholinium-3.

Results

Scopolamine, 0.25 mg/kg i.p. b.d., impaired performance on the T-maze task. The most sensitive measure was % correct responses. It can be seen from FIG. 11 that rats treated with scopolamine do learn to perform on the T-maze, but more slowly than control rats, and without reaching the same peak level of performance.

Figure 11:
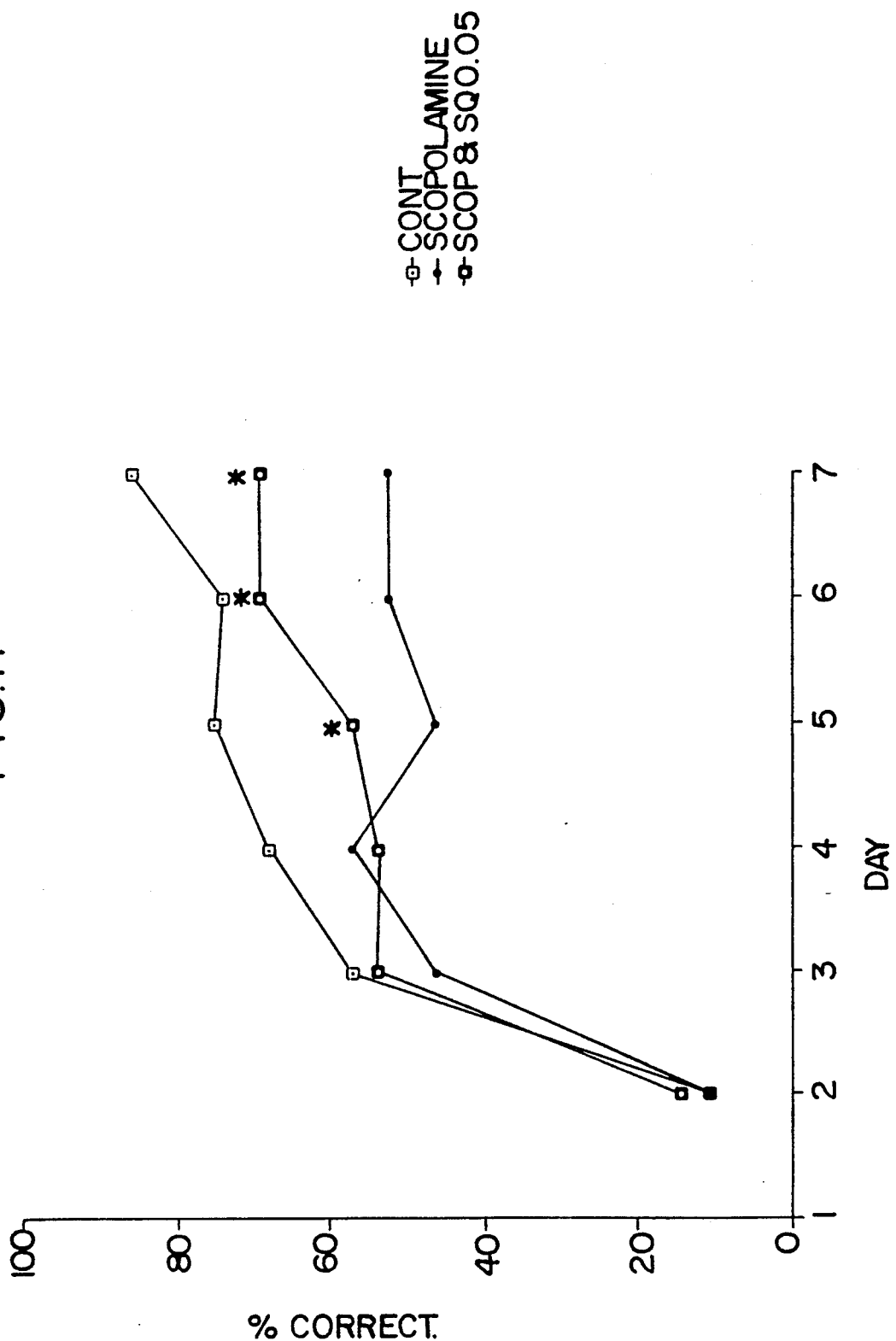
FIGS. 11 and 12 are graphs showing the effect of scopolamine and SQ29,852 on choice performance.
Figure 12:
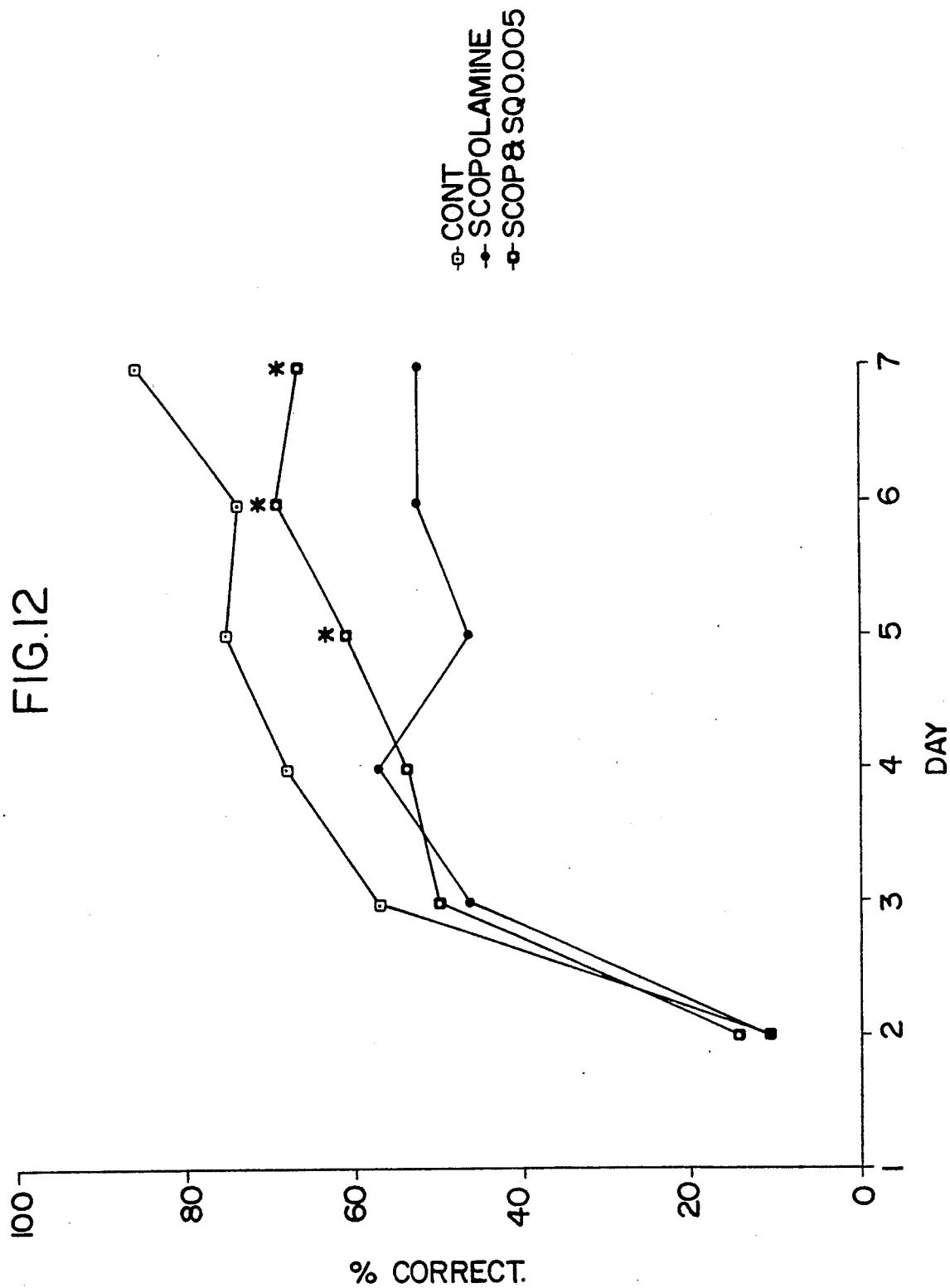

Treatment with SQ29,852 (0.05 mg/kg i.p. b.d.) was shown to antagonize the scopolamine response (* indicates difference from scopolamine alone at the $P<0.05$ significance level, assessed by ANOVA followed by Dunnett's 't' test) (FIG. 11). A lower dose of SQ29,852, 0.005 mg/kg i.p. b.d., was also shown to antagonize the scopolamine deficit (again * indicates significance at the $P<0.05$ level) (FIG. 12).

Figure 13:
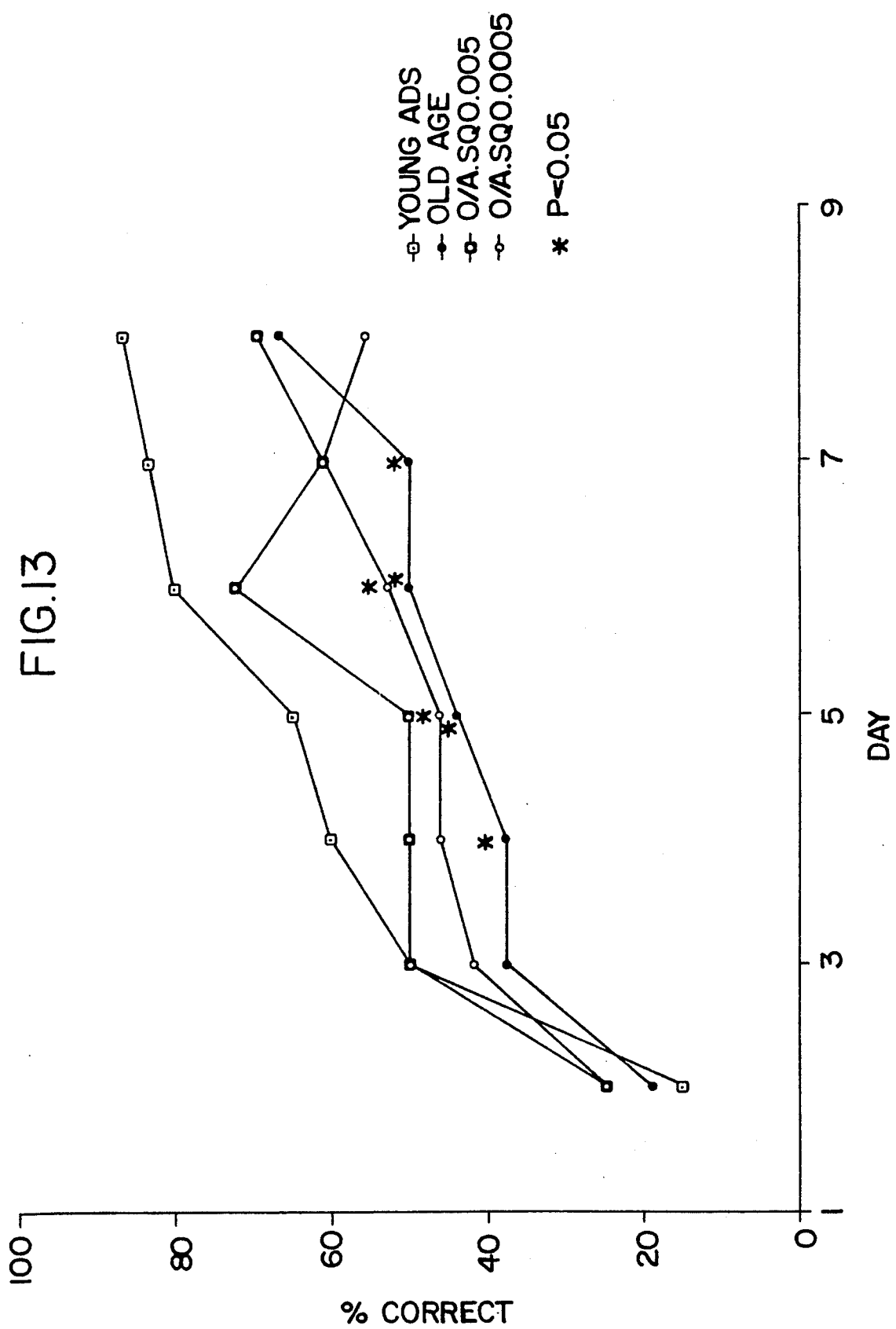
Figure 14:
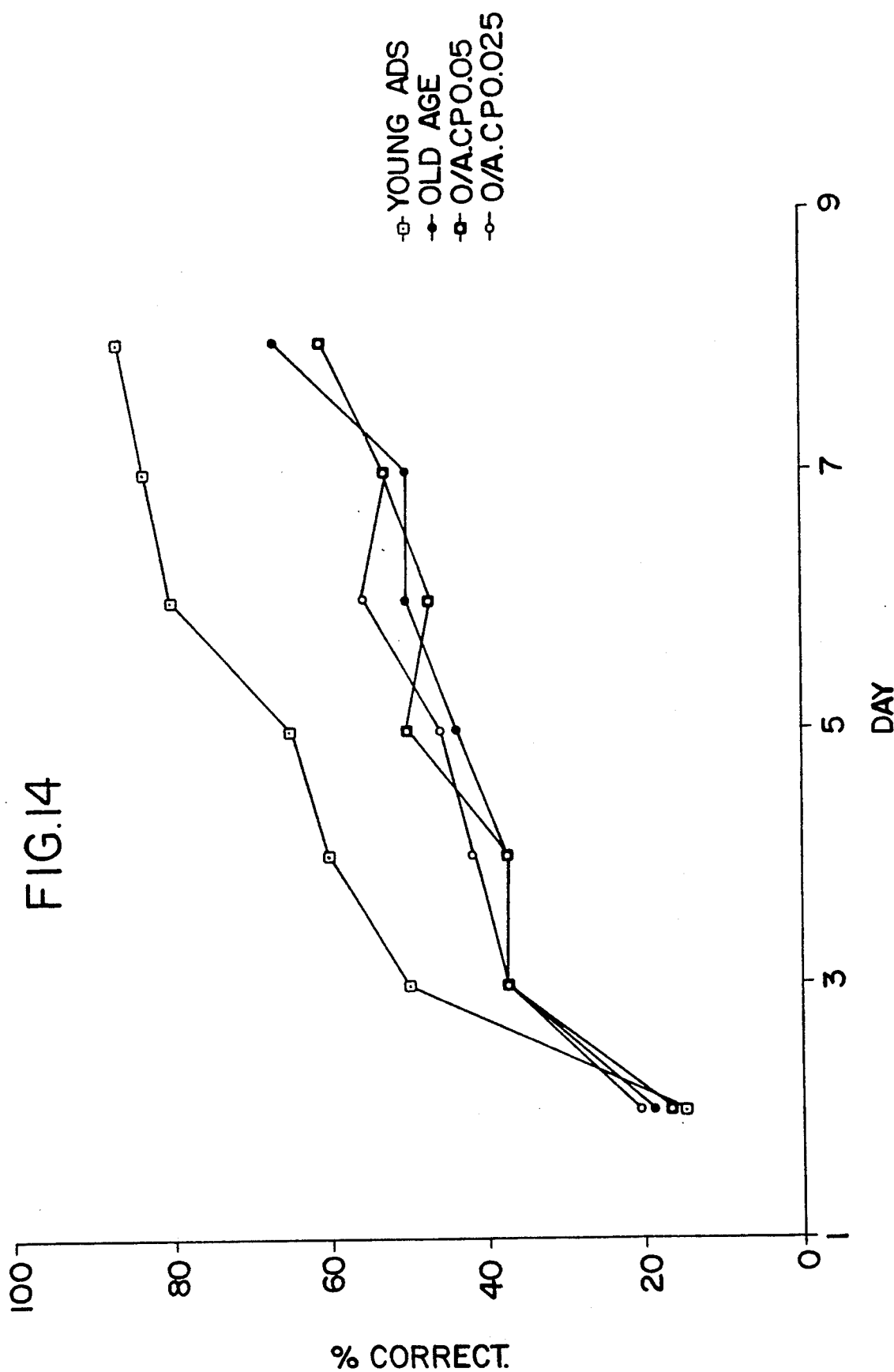

FIG. 13 shows the impaired performance of old age rats as compared with young adult rats (young ads). The difference in performance of the young and old rats was significant to $P<0.05$, the old rats performing to the same low standard as those receiving scopolamine treatment. The impairment in performance of old rats on the T-maze could be antagonized by SQ29,852 at a dose of 0.005 mg/kg i.p. b.d., but not at 0.0005 mg/kg i.p. b.d. (indicated as O/A SQ0.005 and SQ0.0005 on FIG. 13). In contrast to SQ29,852, the impaired performance of aged rats on the T-maze could not be improved by continued treatment with captopril at 0.05 mg/kg I.p. b.d. (O/A CP0.05) or 0.025 mg/kg i.p. b.d. (O/A CP0.025) (FIG. 14).

Whilst % correct responses give the picture of activity of the ACE inhibitors against the impairments of age on the T-maze task, such changes were also detectable on forced latencies and choice latencies. This data is summarized on Tables 1 and 2 (x $\%=\%$ correct responses, $F_L$=forced latency (sec), $C_L$=choice latency (sec).

In the series of experiments where hemicholinium-3 was injected into the cerebral ventricles the performance of rats in the T-maze task was impaired (see FIG. 15, impairment significant to $P<0.05$ at 0.1, 10.0 and 1.0 μg I.C.V.). In preliminary experiments it was shown that the impairment caused by 1.0 μg hemicholinium-3 could be antagonized by SQ29,852 at 0.005 mg/kg i.p. b.d.

Conclusions

The ability of SQ29,852 to antagonize a scopolamine impairment is confirmed in a rat T-maze task. Further, the performance of old age rats on the T-maze could be improved by treatment with SQ29,852, although captopril was not effective at the doses used in the aged animals. This data shows that SQ 29,852 improves cognitive impairments associated with old age.

TABLE 1

| | | Young Adults | Old Age (Vehicle) | Old Age & SQ 0.005 | Old Age & SQ 0.0005 | Old Age & CAPT 0.05 | Old Age & CAPT 0.025 |
|---|---|---|---|---|---|---|---|
| Day 2 | x % = | 15.0 (6.1) | 18.8 (3.1) | 25.0 (6.5) | 25.0 (0) | 16.7 (5.3) | 20.8 (7.7) |
| | $F_L$ = | 282.6 (7.3) | 281.4 (8.5) | 275.9 (9.7) | 269.8 (11.4) | 286.04 (6.6) | 269.6 (13.5) |
| | $C_L$ = | 71.8 (13.8) | 47.5 (11.4) | 57.0 (10.6) | 62.7 (10.1) | 59.0 (16.0) | 55.2 (13.0) |
| Day 3 | x % = | 50.0 (7.9) | 37.5 (7.21) | 50.0 (9.1) | 41.7 (5.3) | 37.5 (10.7) | 37.5 (5.6) |
| | $F_L$ = | 177.7 (16.5) | 255.7 (14.5) | 155.3 (12.1) | 203.4 (13.5) | 214.7 (15.8) | 216.0 (16.3) |
| | $C_L$ = | 43.9 (3.4) | 66.7 (3.70) | 59.5 (5.1) | 65.5 (5.5) | 65.6 (6.6) | 49.9 (5.8) |
| Day 4 | x % = | 60.0 (6.1) | 37.5 (7.2) | 50.0 (6.5) | 45.8 (7.7) | 37.5 (5.6) | 41.7 (5.3) |
| | $F_L$ = | 51.6 (3.1) | 87.6 (4.0) | 45.4 (2.22) | 65.4 (2.9) | 63.3 (2.6) | 66.8 (2.6) |
| | $C_L$ = | 22.6 (0.9) | 36.6 (1.4) | 30.6 (2.3) | 31.5 (1.9) | 37.6 (1.3) | 24.0 (0.94) |
| Day 5 | x % = | 65.0 (6.1) | 43.8 (6.3) | 50.0 (6.5) | 45.8 (7.7) | 50.0 (6.5) | 45.8 (9.4) |
| | $F_L$ = | 25.2 (1.5) | 56.1 (3.2) | 33.9 (2.4) | 59.2 (2.6) | 49.2 (2.1) | 45.1 (2.14) |
| | $C_L$ = | 20.9 (0.7) | 22.6 (0.97) | 28.0 (1.6) | 2.9 (1.1) | 25.6 (0.9) | 19.7 (1.1) |
| Day 6 | x % = | 79.9 (3.3) | 50.0 (6.8) | 72.2 (3.5) | 52.7 (6.7) | 47.2 (2.8) | 55.6 (7.1) |
| | $F_L$ = | 28.3 (1.3) | 42.2 (1.5) | 23.9 (0.9) | 25.5 (0.9) | 26.6 (1.5) | 24.7 (0.84) |
| | $C_L$ = | 18.4 (1.1) | 14.3 (1.3) | 15.7 (0.8) | 16.9 (1.1) | 14.3 (0.9) | 15.2 (0.8) |
| Day 7 | x % = | 83.3 (5.3) | 50.0 (6.8) | 61.1 (5.6) | 61.1 (3.5) | 52.8 (2.8) | 52.7 (0.8) |
| | $F_L$ = | 17.7 (0.75) | 26.9 (0.8) | 23.3 (1.1) | 24.9 (1.01) | 21.7 (0.84) | 23.8 (1.1) |
| | $C_L$ = | 9.4 (0.7) | 15.9 (1.3) | 13.7 (0.7) | 21.8 (0.9) | 17.1 (1.1) | 18.2 (0.95) |
| Day 8 | x % = | 86.6 (3.3) | 66.7 (6.8) | 69.5 (2.8) | 55.7 (3.5) | 61.1 (5.6) | 61.1 (3.5) |
| | $F_L$ = | 20.4 (1.2) | 27.1 (1.3) | 27.1 (1.1) | 26.9 (1.01) | 30.5 (2.4) | 24.7 (0.95) |
| | $C_L$ = | 8.1 (0.5) | 18.0 (0.9) | 13.7 (0.6) | 16.1 (0.91) | 13.8 (0.62) | 12.5 (0.42) |

EXAMPLE 11

The following experiments were carried out to demonstrate the effects of the ACE inhibitors SQ29,852 and captopril in rodent tests of cognition.

METHOD

Experimental animals

Male albino B.K.W. mice (25–30 g, 6 to 8 weeks old i.e. "young adult") and (33–38 g 8 to 10 months old i.e. "aged") were housed in groups of 10 and given free access to food and water. Mice were kept on a 12 hour light/dark cycle with lights off at 8:00 am.

Male Lister Hooded rats (250–300 g, 11 to 15 weeks old i.e. "young adult", and 350–400 g 13 to 17 months old i.e. "aged") were housed in groups of 5 and given free access to food and water ad libitum or until the start of behavior testing (see below). Rats were kept on a 12 hour light/dark cycle with lights off at 9.00 hour. The temperature was maintained at 21°±1° C.

Mouse Habituation test

Testing was carried out daily between 08.30 and 12.30 hour. Mice were taken from a dark home environment in a dark container to the experimental room maintained in low red lighting, and placed into the center of the white section of a white and black test box. The box (45×27×27 cm high) was divided. 40% of the area was painted black and illuminated under a red light (60W, 0Lux) and the other painted white and brightly illuminated with a white light (1×60W, 400 Lux) located 17 cm above the box. Access between the two areas was enabled by a 7.5×7.5cm opening located at floor level in the center of the partition. Behavior was assessed via remote video-recording and the latency to move from the white to the black section was measured. The brightly lit area of the black and white test box has mildly aversive properties, mice normally distributing their behavior preferentially in the black compartment (Costall, B., et al, J. Pharm. Pharmac. 40:495–500, 1988). On repeated daily testing mice habituate to the test system with a reduced latency in movement from the white to the black section.

T-maze reinforced alternation performance in rats

Animals were trained on a food reinforced alternation task using a modification of the protocol of Salamone et al., Behav. Brain Res. 13:63–70 (1982). Food was withdrawn 2 days prior to testing and animals were deprived of food for 23 hours/day. Water was available ad libitum and body weight was maintained at 85%. Animals were taken from the holding room to the dimly lit test room 30 minutes before testing. Experiments were carried out between 08.00 and 15.00 hour using an elevated T-maze. The start arm measured 80 cm×10 cm and the side arms were 60cm ×10cm with food wells 3 cm deep at each end. The T-maze was elevated 30 cm above the ground.

On day 1 each rat was allowed 10 minutes habituation to the maze. Both food wells were baited with banana flavored pellets and pellets were also scattered along the approach arm. The rats were then subject to a period of reinforced alternation training, days 2–5 being designated "pre-training" days with days 6–9 "training" days. All reinforced alternation training consisted of paired trials (each pair consisting of a 'run'). The first trial was the 'forced' trial in that one arm was blocked whilst the other arm was baited. The second trial of the pair was a "choice" trial in which reward pellets were placed in the arm opposite to that reinforced in the first trial of the pair. A correct choice was when the rat entered the arm and passed a point 20 cm along the arm containing the food in the choice trial. In-addition to correct/incorrect choice, latency to reward was recorded for both forced and choice trials.

4 runs/day were carried out on pretraining days (inter-trial interval 0s, inter-run interval 30s) and 6 runs/day during training (inter-trial interval 30s; inter-run interval 60 sec). The number of lefts and rights was random (following Gellerman Schedule) and was balanced across the test groups.

Water-Maze performance in rats

Rats were placed in a square (120cm×120cm) pool of water which contained a white painted platform located 2cm below the surface of the water. The water was rendered opaque by the addition of a small quantity of emulsion to obscure the presence of the platform. The rats were trained to locate and escape onto the island using spatial strategies. A two day test protocol was utilized and was a modification of the method of Morris, J. Neurosci. Meth. 11:47–60.

Day 1

Each rat was placed on the island for 30 sec. immediately before testing commenced. The island was kept in a constant position for each rat (the position was randomized and balanced across the groups) but each rat began each trial at a different corner in the pool (the positions balanced across the groups). A training trial began with the animal being lowered into the pool, the animal close to and facing the corner designated for the trial. The timer and tracking device was-started and the time recorded for the animal to escape from the water onto the platform. The rat remained on the platform for 10 sec. before being placed in the pool for trial 2. On each trial the rat was allowed a maximum 100 sec. to find the island and the latency, swim speed and % time spent in the island quadrant were measured. If the rat failed to find the island in 100 sec. it was placed on it for 10 sec. and then removed. Each rat received 6 trials on day 1. A 7th trial with a black visible island was also carried out to ensure that no visual/locomotor effects were influencing performance.

Day 2

The same procedure was carried out as that of day 1, the basis of the test being that rats had formed a strategy to find the island on day 1 which could be disrupted by drug treatments.

Statistical Analysis

Data was analyzed by 2 way analysis of variance (ANOVA) with repeated measures and/or Dunnett's t-test as indicated in the results section.

Drugs

Scopolamine HBr and N-methyl scopolamine HBr (Sigma), SQ29,852 [(5)-1-[6-amino-2[hydroxy-(4-phenylbutyl)phosphinyl]oxy)-1-oxohexyl]-L-proline-]and captopril (Squibb) were all dissolved in normal saline. Doses of drugs are expressed as the base. All drugs were administered in a volume of 1 ml/kg (rat) or 1 ml/100 g (mouse) body weight by the intraperitoneal route. Dose schedules are indicated in the results section.

RESULTS

Mouse habituation test

Habituation profile of young adult and aged mice

Naive young adult and aged mice placed into the center of the white section of the black and white test box moved within 10 to 12 sec into the black section. On daily testing young adult animals habituated to the test system, moving by the 5th day within 2 to 4 sec into the black section. In contrast, the slight reduction of some 10% in the latency of movement of aged mice into the black section over the 7 day period failed to achieve significance (FIG. 16).

Influence of captopril and SQ29,852 on basal learning and scopolamine impairment In preliminary studies doses of captopril (0.05 mg/kg b.d.) and SQ29,852 (0.0005 mg/kg b.d.) were carefully selected as the lowest doses capable of influencing the latency of movement on continued treatment. This avoided the possibility of the use of doses of captopril and SQ29,852 that might have an acute effect to directly modify aversive responding or exploratory behavior in the black and white test box, to obscure an interpretation of the present results.

Figure 16C:
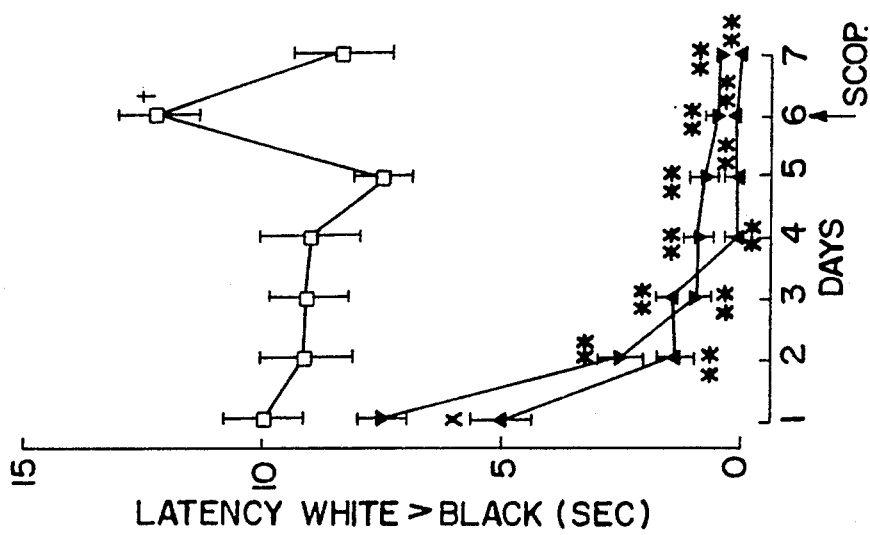
FIG. 16 is a graph showing the effect of captopril and SQ29,852 to enhance mouse habituation responding in a black and white test box, and to prevent a scopolamine induced impairment.
Figure 16B:
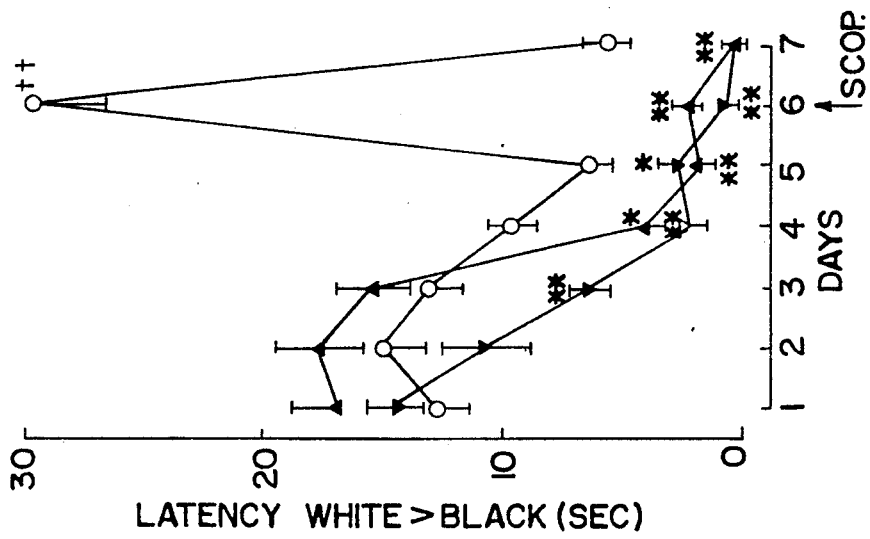
Figure 16A:
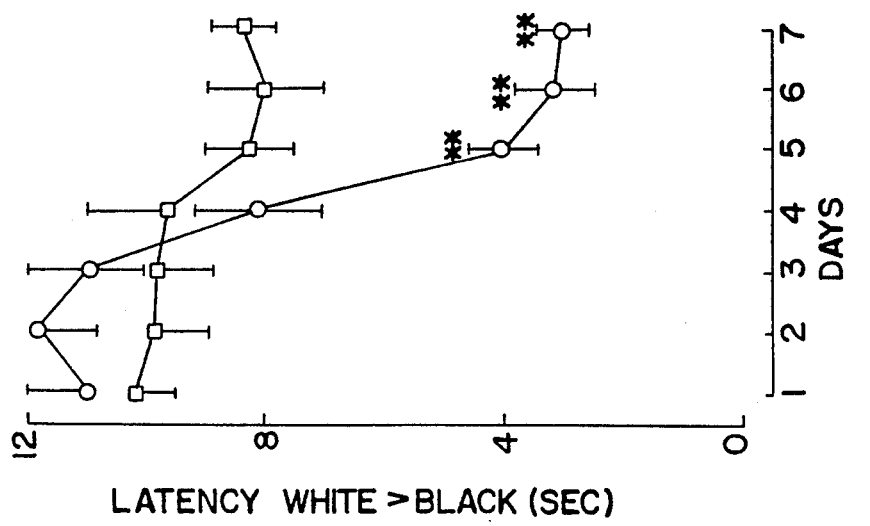

FIG. 16 shows the effect of captopril and SQ29,852 to enhance mouse habituation responding in a black and white test box, and to prevent a scopolamine induced impairment. In A. young adult (0-0) and aged (□-□) mice received vehicle injections, B. young adult mice received injections of vehicle (0-0), captopril (0.05 mg/kg i.p. b.d. (∇-∇) or SQ29,852 (0.0005 mg/kg i.p. b.d. (Δ-Δ) and C. aged mice received injections of vehicle (□-□), captopril (0.05 mg/kg i.p. b.d. (∇-∇) or SQ29,852 (0.0005 mg/kg i.p. b.d. (Δ-Δ). In B. and C. animals receiving vehicle or drug injections were challenged with a single treatment of scopolamine (Scop. 0.25 mg/kg i.p. B, 0.1 mg/kg i.p. C.) on the 6th day [↑]. Significant differences in the latency of initial movement from the white to the black area between A. aged and young adult mice and B., C. drug treatments with captopril and SQ29,852 compared to control (vehicle) values are indicated $*P<0.01$ and $**P<0.001$ (Dunnett's t test); a significant increase in the latency of movement induced by scopolamine relative to vehicle controls is indicated $+P<0.05$ and $++P<0.001$ (Dunnett's t test).

In young adult mice, the daily treatment with captopril and SQ29,852 enhanced habituation to the test system, reducing the latency of movement into the black section by the 3rd or 4th day (FIG. 16). The administration of scopolamine (0.25 mg/kg) to the young adult mice on the 6th day impaired habituation to the test box, increasing the latency of movement into the black section 2 fold. Captopril and SQ29,852 prevented the effect of scopolamine (FIG. 16).

In aged mice, the daily treatment with captopril and SQ29,852 reduced the latency of movement into the black section. Even on the first day of testing mice moved more quickly than untreated animals into the black section and this achieved significance using SQ29,852. Habituation to the test box occurred rapidly, by the 3rd day animals moving into the black section within 1 to 3 sec and, by the 4th day of treatment, animals receiving captopril or SQ29,852 moved into the black either immediately or within 1 or 2 sec. The administration of scopolamine (0.1 mg/kg) on the 6th day of testing caused a significant but modest delay in movement into the black section as compared to the response obtained on the previous day. This impairment was not observed in mice receiving treatment with captopril or SQ29,852 (FIG. 16).

FIG. 17 shows the effects of captopril and SQ29,852 on scopolamine induced impairment in a T-maze reinforced alternation task in the rat. Young adult animals were given captopril alone (□ - - □, 1.0 mg/kg i.p. b.d.), SQ29,852 alone (□ - - □, 1.0 mg/kg i.p. b.d.) or vehicle (□-□), scopolamine (0-0), 0.25 mg/kg i.p. b.d.) or scopolamine plus captopril or SQ29,852 (   mg/kg i.p. b.d. doses indicated) for 9 days and data is presented following a 1 day habituation to the test apparatus. Data obtained was analyzed by two-way ANOVA followed by Dunnett's t-test, n=10. A significant antagonism by SQ29,852 of the scopolamine induced impairment is indicated $*P<0.05$ and $**P<0.01$; a significant impairment in choice performance induced by scopolamine relative to vehicle controls was obtained at $P<0.05$–$0.001$ on all other non-starred values.

Scopolamine induced disruption of reinforced alternation performance was characterized by significant reduction in the % correct responses (see below). A dose of 0.25 mg/kg i.p. b.d. scopolamine was selected as the minimal dose causing a maximal reduction of some 60% correct responses compared to vehicle controls (FIG. 17). N-methylscopolamine (0.25 mg/kg i.p. b.d.) was ineffective. SQ29,852 (0.005–0.5 mg/kg i.p. b.d.) antagonized the scopolamine induced impairment and at 0.005 and 0.05 mg/kg i.p. b.d. the choice performance indicated by % correct response was not significantly different from that of vehicle control animals (two factor ANOVA with repeated measures, Factor A = drug treatments and Factor B = time in days) revealed significant effects of drug (F, (4, 24) = 56.34 $P<0.01$, time (F, (7.42) = 25.31 $P<0.01$ and a significant drug×time interaction F, (28, 168) = 1.03 $P<0.05$; further data analysis using Dunnett's t test revealed significant effects of scopolamine and the antagonism of these effects by SQ29,852, see FIG. 17). Lower and higher doses of SQ29,852 (0.0005 and 1.0 mg/kg i.p. b.d.) were ineffective in this model (FIG. 17). Captopril (0.1 and 1.0 mg/kg i.p. b.d.) failed to antagonize the scopolamine induced impairment but at 1.0 mg/kg b.d. delayed the onset of impairment as seen by a non-significant change from control values on days 1 and 2 of treatment (two factor ANOVA, Factor A = drug treatment and Factor B = time in days) revealed significant effect of drug (F, (4, 24) = 39.61, $P<0.01$) and time (F, (7, 42) = 13.82 $P<0.01$) and significant drug×time interaction (F, (28, 168) = 1.79 $P<0.05$); further data analysis using Dunnett's t test revealed effects to be significant (see FIG. 17). Both captopril (1.0 mg/kg i.p. b.d.) and SQ29,852 (1.0 mg/kg i.p. b.d.) administered alone failed to modify basal performance (FIG. 17).

Effects of captopril and SQ29,852 on performance of aged rats in a T-maze reinforced alternation task FIG. 18 shows the effect of captopril and SQ29,852 in aged rats in a T-maze reinforced alternation task. Aged rats received daily treatment with captopril or SQ29,852 (   , mg/kg i.p. b.d. doses indicated) or vehicle (□-□) for 9 days, young adult rats were used as a 'reference control' and received vehicle (0-0), and data is presented following a 1 day habituation to the test apparatus. Data obtained was analyzed by two-way ANOVA followed by Dunnett's t-test, n=7-10. A significant improvement in choice performance induced by SQ29,852 in aged rats compared to vehicle treated aged rat controls is shown $*P<0.05$.

Aged rats showed a reduction in choice performance of some 30% compared to the performance of young adult animals as assessed using two-way ANOVA followed by Dunnett's t test (see below). The reduced performance of aged rats was significantly improved by treatment with SQ29,852 (0.005 mg/kg i.p. b.d.), the deficit between the young adult and aged animals being reduced by 50%. However, the more modest improvements of 20 to 30% observed using 0.0005 and 0.05 mg/kg SQ29,852 did not achieve significance, and higher doses were ineffective in this test (two factor ANOVA, with repeated measures, Factor A = age/drug treatment, Factor B = time in days) revealed significant effects of age/drug (F, (5, 30) = 16.78 p<0.01) and time (F, (7, 42) = 27.85 P<0.01); further data analysis using Dunnett's test revealed significant effects between the test groups (see FIG. 18). Captopril (0.025-1.0 mg/kg i.p. b.d.) failed to modify choice performance in aged rats (F IG. 18). Latency to reward was not modified by treatment with captopril or SQ29,852 in either young adult or aged rats.

Figure 19:
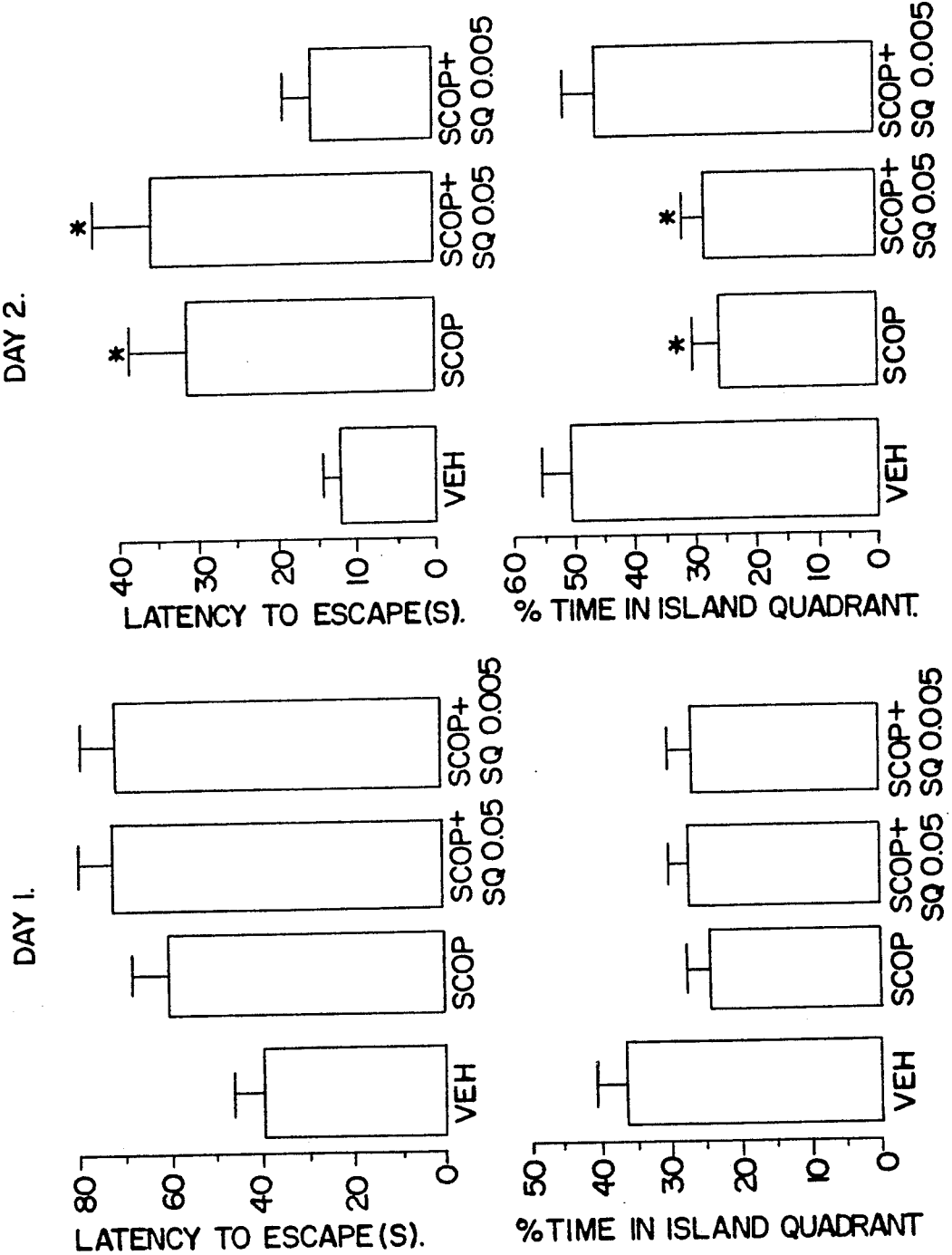
FIG. 19 is a graph showing the effect of SQ29,852 to inhibit scopolamine-induced impairment of rat behaviour in the water-maze test.

Effect of SQ29,852 on scopolamine induced impairment of rat performance in the water maze FIG. 19 shows the effect of SQ29,852 to inhibit scopolamine induced impairment of rat behavior in the water-maze test. Rats received scopolamine (0.25 mg/kg i.p. b.d.), scopolamine plus SQ29,852 (0.005 and 0.05mg/kg i.p. b.d.) or vehicle and the latency to escape from the water onto an island, and the % time spent in the island quadrant were measured in 6 trials on the first and second day. Each value is the mean ±S.E.M. of 6 determinations. S.E.M.s for values for % time in island quadrant were calculated from original data. The significance of scopolamine/drug treatments to impair performance as compared to vehicle controls, and the ability of SQ29,852 to inhibit the effects of scopolamine is indicated by *P<0.05 (Dunnett's t-test).

On the first day of testing the trend for scopolamine (0.25 mg/kg i.p. b.d.) to increase the escape latency failed to achieve significance. The trend for the administration of scopolamine alone, or in combination with SQ29,852 to reduce the % time in the island quadrant also failed to achieve significance. On the second day, the continued treatment with scopolamine significantly impaired the escape latency by 62% and % time in the island quadrant by 40%. SQ29,852 (0.005 mg/kg i.p. b.d.) significantly antagonized the scopolamine induced deficit such that the performance to escape and the % time in the island quadrant were indistinguishable from values determined for vehicle treated control animals. The higher dose of SQ29,852 (0.05 mg/kg i.p. b.d.) failed to modify the scopolamine induced impairment in this test. The lack of effect of drug treatments on swim speed and the ability to locate the black visible island indicated an absence of effect on visual and locomotor performance.

DISCUSSION

In the present Example, the ACE inhibitors captopril and SQ29,852 were shown to enhance performance in tests of cognitive function in the rodent. Using a two compartment light/dark test box to measure habituation in young adult mice, the mildly aversive brightly lit environment ensured that mice placed into the white brightly lit area would move into the black section. On repeated daily testing an habituation to the procedure was apparent by the 3rd to 5th day, mice moving with a reduced latency into the black environment. Treatment with either captopril or SQ29,852 facilitated the habituation response by the 3rd to 4th day of testing, and such treatments antagonized the impairment caused by the administration of scopolamine.

Aged animals perform less well in tests of cognitive function (Bartus, R. T., et al., Science 217:408-417, 1982) and aged mice failed to habituate to the test procedure, although their initial performance was comparable to that of young adult mice, indicating that the impairment was not the consequence of a slowness in movement. Aged animals also proved more sensitive to the toxic effects of scopolamine necessitating the use of a lower dose which, nevertheless, was sufficient to induce an impairment in performance. Aged mice treated with captopril or SQ29,852 showed a rapid habituation response evident by the first or second day of treatment, and the habituation pattern was not disrupted by scopolamine. Therefore, as found in the young adult mice, captopril and SQ29,852 can also prevent the impairments caused by scopolamine in aged mice. The habituation response of aged mice treated with captopril or SQ29,852 was achieved significantly more rapidly than in young adult animals, with or without treatment with captopril or SQ29,852.

SQ29,852 was also found to modify cognitive performance of the rat. In rats trained on a reinforced alternation paradigm in the T-maze, aged rats showed a 30% reduction in choice performance as compared to young adults, and there was no evidence that the choice deficit in the older animals was due to a reduced motor performance. The ability of SQ29,852 to antagonize the performance deficit in aged rats, and the impairment induced by scopolamine in young adult rats, was observed as a bell-shaped dose response curve. Captopril's only effect in the T-maze test was to delay the scopolamine induced impairment on the first and second day of treatment. In the water maze procedure, scopolamine impaired escape latency and % time in the island quadrant and the disruptions in performance were antagonized by a 2 day treatment with SQ29,852 at a low dose, but not at a higher dose.

The cognitive deficits associated with scopolamine use in animals and man have been linked with a central cholinergic blockade (Bartus, R. T., et al, supra). Angiotensin II may cause a similar change but by a different mechanism to inhibit the release of acetylcholine from cholinergic neurones (Barnes, J. M., et al, Brain Res. in press). In the latter 'in vitro' study using slices of rat entorhinal cortex angiotensin I was shown to be ineffective, and it was suggested that, by inhibiting ACE, captopril and SQ29,852 may remove a tonic inhibitory influence of angiotensin II on the cholinergic neurone. In the mouse test SQ29,852 was at least one hundred times more potent than captopril and is two orders of magnitude more potent to inhibit ACE (Barnes, J. M et al., unpublished data). The increase in release of acetylcholine could enhance basal performance or act to oppose the scopolamine induced acetylcholine receptor blockade. Such a hypothesis is in agreement with literature reporting that cholinergic agents can improve performance in cognitive tests (Bartus, R.T., et al supra). However, in the rodent behavioral tests both captopril and SQ29,852 were effective at exceptionally small doses, doses that may be less than required to inhibit ACE, at least as measured in body tissues. Sudilovsky et al., (Soc. Neurosci. Abstract, Vol. 14, 1988) have reported a reversal by neloxone of the captopril-induced delay in the extinction of a conditioned avoidance response in the rat. It remains relevant that epicaptopril, which lacks ability to inhibit ACE, fails to modify performance in the rodent models of cognitive performance (Costall, B., et al., unpublished data).

The effects of SQ29,852 were observed in the rat over a narrow dose range, and there is no immediate explanation as to why the effects of SQ29,852 should decrease with increase in dose. However, if the effects of SQ29,852 are mediated via a cholinergic mechanism, it may be relevant that cholinergic agents in their own right appear to improve cognitive performance within a narrow dose range (Bartus, R.T., et al, supra).

In summary, both captopril and SQ29,852 in the rodent can improve performance in tests of cognition. SQ29,852 is particularly potent in such tests. The ACE inhibitors captopril and SQ29,852 enhanced a habituation response to bright illumination in young adult and aged mice measured in a two compartment light/dark test box. The treatments also antagonized a scopolamine induced impairment and SQ29,852 was approximately 100 times more potent than captopril. In rats trained on a reinforced alternation paradigm in a T-maze, aged rats, as compared to young adults, showed a reduction in choice performance which was antagonized by SQ29,852. The impairment in choice performance in the T-maze induced by scopolamine in young adult rats was antagonized by SQ29,852 whilst captopril only delayed the onset of the scopolamine induced impairment. SQ29,852 also antagonized scopolamine impaired escape latency in a spatial learning/memory paradigm in a water-maze test. The effects of SQ29,852 in the rat were achieved within a restricted dose range. The ability of captopril and SQ29,852 to increase performance in the behavioral tests is discussed in terms of an antagonism of angiotensin converting enzyme to remove an inhibitory role of angiotensin II on central cholinergic function.

Examples 12 to 17

SQ 29,852 formulations suitable for oral administration in inhibiting loss of cognitive functions are set out below.

1000 tablets each containing 2.5 to 80 mg of SQ 29,852 were produced from the following ingredients.

another 30% portion of the tricalcium phosphate and another ¼ portion of the microcrystalline cellulose were added to the above mix while continuing mixing for 2 to 5 minutes. The remaining tricalcium phosphate, microcrystalline cellulose and crospovidone were added to the above mix while continuing mixing for 2 to 5 minutes. Magnesium stearate was added to the above mix and mixing was continued for 2 to 5 minutes. The resulting mixture was then compressed in a tablet press to form 1000 tablets of each of 2.5, 5.0, 10.0, 20.0, 40.0, and 80.0 mg formulations which are used for inhibiting loss of cognitive function.

What is claimed:

1. A method of inhibiting loss of cognitive function in a mammalian specie over a prolonged period of time, which comprises administering to a mammalian specie in need of such treatment an effective amount of an angiotensin converting enzyme inhibitor which is (S)-1-[6-amino-2-[hydroxy(4 phenylbutyl)phosphinyl]oxy]-1-oxohexyl]-L-proline (SQ29,852), over a prolonged period of treatment to inhibit loss of cognitive function during such period of treatment.

2. The method as defined in claim 1 wherein said angiotensin converting enzyme inhibitor is administered orally or parenterally.

3. The method as defined in claim 1 wherein said angiotensin converting enzyme inhibitor is admixed with a pharmaceutically acceptable carrier therefor.

4. The method as defined in claim 1 wherein said angiotensin converting enzyme inhibitor is administered in the form of tablets, capsules or by injection.

5. The method as defined in claim 1 wherein said angiotensin converting enzyme inhibitor is [(S) 1-[6-amino 2-[[hydroxy(4-phenylbutyl)phosphinyl]oxy]-1-oxohexyl-L-proline and is] administered systematically in an amount of from about 0.1 to about 500 mg/1 or 4 times a day.

| | COMPOSITION OF SQ29, 852 TABLETS (Tricalcium Phosphate Formulation) | | | | | |
|---|---|---|---|---|---|---|
| | Example 12 g/1000 tablets | Example 13 g/1000 tablets | Example 14 g/1000 tablets | Example 15 g/1000 tablets | Example 16 g/1000 tablets | Example 17 g/1000 tablets |
| SQ29, 852 | 2.50 (2.5 mg/ tablet) | 5.0 (5.0 mg/ tablet) | 10.0 (10.0 mg/ tablet) | 20.0 (20.0 mg/ tablet) | 40.0 (40.0 mg/ tablet) | 80.0 (80.0 mg/ tablet) |
| Tribasic Calcium Phosphate, NF | 34.13 | 56.0 | 112.0 | 102.0 | 143.0 | 70.0 |
| Microcrystalline Cellulose, NF* | 35.00 | 34.5 | 69.0 | 69.0 | 103.5 | 41.0 |
| Crospovidone, NF | 2.62 | 3.5 | 7.0 | 7.0 | 10.5 | 7.0 |
| Magnesium Stearate, NF | 0.75 | 1.0 | 2.0 | 2.0 | 3.0 | 2.0 |
| TOTAL | 75 | 100 | 200 | 200 | 300 | 200 |

*Preferred brand/grade-Avicel PH 102.

SQ 29,852 (screened through a 30 mesh screen), about 30% of the tricalcium phosphate, about ⅓ of the crospovidone and about ¼ of the microcrystalline cellulose were mixed together for about 2–5 minutes. Thereafter,

UNITED STATES PATENT AND TRADEMARK OFFICE
CERTIFICATE OF CORRECTION

PATENT NO. : 5,015,633
DATED : May 14, 1991
INVENTOR(S) : Abraham Sudilovsky

It is certified that error appears in the above-identified patent and that said Letters Patent is hereby corrected as shown below:

Column 30, line 19, please insert a bond (-) between "4" and "phenylbutyl";

line 33, please insert a bond (-) between "(S)" and "1";

line 34, please insert a bond (-) between "amino" and "2";

line 55, please change "or" to --to-- .

Signed and Sealed this

Twenty-sixth Day of January, 1993

Attest:

STEPHEN G. KUNIN

*Attesting Officer*  *Acting Commissioner of Patents and Trademarks*